(12) United States Patent
McLane et al.

(10) Patent No.: US 12,262,973 B1
(45) Date of Patent: Apr. 1, 2025

(54) SYSTEMS AND METHODS OF A MEDICAL DEVICE AND ENVIRONMENTAL CONNECTIVITY HUB

(71) Applicant: PERIN HEALTH DEVICES LLC, Oklahoma City, OK (US)

(72) Inventors: Ian McLane, Bell Canyon, CA (US); Christopher Smith, Thousand Oaks, CA (US)

(73) Assignee: Perin Health Devices LLC, Oklahoma City, OK (US)

( * ) Notice: Subject to any disclaimer, the term of this patent is extended or adjusted under 35 U.S.C. 154(b) by 0 days.

(21) Appl. No.: 18/807,373

(22) Filed: Aug. 16, 2024

Related U.S. Application Data

(60) Provisional application No. 63/573,306, filed on Apr. 2, 2024, provisional application No. 63/572,012, filed on Mar. 29, 2024.

(51) Int. Cl.
*A61B 5/00* (2006.01)
*A61B 5/08* (2006.01)
(Continued)

(52) U.S. Cl.
CPC .......... *A61B 5/0022* (2013.01); *A61B 5/0823* (2013.01); *A61B 5/7203* (2013.01);
(Continued)

(58) Field of Classification Search
CPC ... A61B 5/0022; A61B 5/0823; A61B 5/7203; A61B 5/7264; A61B 7/003; A61B 2560/0242; G06F 21/602; G06F 21/6245
(Continued)

(56) References Cited

U.S. PATENT DOCUMENTS 6,681,003 B2 * 1/2004 Linder ................ G16H 40/67
379/106.02
8,126,728 B2 * 2/2012 Dicks ................ G16H 40/67
710/16
(Continued)

OTHER PUBLICATIONS

C. Contasel, D.-C. Tranca, A.-V. Palacean, and D. Rosner, "Increasing communication security for Bluetooth Medical Devices in eHealth systems," in 2022 21st RoEduNet Conference: Networking in Education and Research (RoEduNet), Sep. 2022, pp. 1-4. doi: 10.1109/RoEduNet57163.2022.9921104.
(Continued)

*Primary Examiner* — Michael Tomaszewski
(74) *Attorney, Agent, or Firm* — Command IP LLP; Pejman Yedidsion

(57) ABSTRACT

Systems, devices, and methods including a processor having addressable memory, where the processor is configured to: collect, via a set of sensors, biological signals related to patient status; collect, via an environmental monitoring device, environmental data associated with an environment of the patient; store, locally via a secure encrypted local database, the collected biological signals and the collected environmental data; detect an abnormality in the collected biological signals; increase measurement frequency of the biological signals by the set of sensors based on the detected abnormality; detect an error in the collected biological signals; determine whether the detected error in the collected biological signals of the current reading is due to environmental factors; correct the determined error in the collected biological signals; and transmit the error corrected collected biological signals as encrypted data.

18 Claims, 12 Drawing Sheets

(51) Int. Cl.
    *A61B 7/00*         (2006.01)
    *G06F 21/60*      (2013.01)
    *G06F 21/62*      (2013.01)

(52) U.S. Cl.
    CPC ............ *A61B 5/7264* (2013.01); *A61B 7/003* (2013.01); *G06F 21/602* (2013.01); *G06F 21/6245* (2013.01); *A61B 2560/0242* (2013.01)

(58) Field of Classification Search
    USPC ........................................................ 705/2–3
    See application file for complete search history.

(56) References Cited

U.S. PATENT DOCUMENTS

| | | | |
|---|---|---|---|
| 8,687,554 B2 * | 4/2014 | Simons | G16H 40/67 |
| | | | 370/328 |
| 8,957,777 B2 * | 2/2015 | Baker | H04W 84/18 |
| | | | 340/539.3 |
| 9,402,545 B2 * | 8/2016 | Baker | A61B 5/0002 |
| 9,526,421 B2 * | 12/2016 | Papadopoulos | G16H 20/70 |
| 9,848,058 B2 * | 12/2017 | Johnson | H04L 67/52 |
| 9,872,087 B2 * | 1/2018 | DelloStritto | H04L 67/12 |
| 10,004,451 B1 | 6/2018 | Proud | |
| 10,178,953 B2 | 1/2019 | Ji et al. | |
| 10,230,783 B2 | 3/2019 | Rajan et al. | |
| 10,426,358 B2 | 10/2019 | Barnett, Jr. et al. | |
| 10,433,726 B2 | 10/2019 | Ramesh et al. | |
| 10,542,889 B2 | 1/2020 | Ramesh et al. | |
| 10,716,534 B1 | 7/2020 | Mclane et al. | |
| 10,732,600 B2 | 8/2020 | Sinha et al. | |
| 10,743,091 B1 | 8/2020 | Wang et al. | |
| 11,581,099 B1 | 2/2023 | Rufo et al. | |
| 11,680,935 B2 | 6/2023 | Martin | |
| 2006/0036619 A1 * | 2/2006 | Fuerst | G16H 50/80 |
| 2008/0215627 A1 * | 9/2008 | Higgins | G16H 10/60 |
| 2008/0294020 A1 * | 11/2008 | Sapounas | A61B 5/0022 |
| | | | 600/301 |
| 2013/0131465 A1 * | 5/2013 | Yamamoto | A61B 5/7271 |
| | | | 600/300 |
| 2013/0132109 A1 * | 5/2013 | Mruthyunjaya | G16H 70/60 |
| | | | 705/2 |
| 2018/0027077 A1 * | 1/2018 | Melodia | G16H 40/67 |
| | | | 370/254 |
| 2019/0046037 A1 * | 2/2019 | Ramesh | G16H 50/20 |
| 2020/0186378 A1 * | 6/2020 | Six | H04L 12/2803 |
| 2020/0271488 A1 * | 8/2020 | Tanutama | G01D 18/00 |
| 2021/0151164 A1 * | 5/2021 | Macary | A61M 21/02 |
| 2022/0059216 A1 * | 2/2022 | Lewis | H04W 4/80 |
| 2022/0122735 A1 * | 4/2022 | Sherkat | G06N 3/04 |
| 2022/0215952 A1 * | 7/2022 | Bourouis | G06F 21/645 |
| 2022/0296169 A1 * | 9/2022 | Alghorani | A61B 5/0024 |
| 2023/0114515 A1 * | 4/2023 | Tee | G16H 80/00 |
| | | | 705/3 |
| 2024/0371496 A1 * | 11/2024 | Wang | A61B 5/0002 |

OTHER PUBLICATIONS

C.-T. Yang, S.-T. Chen, W. Den, Y.-T. Wang, and E. Kristiani, "Implementation of an Intelligent Indoor Environmental Monitoring and management system in cloud," Future Generation Computer Systems, vol. 96, pp. 731-749, Jul. 2019, doi: 10.1016/j.future.2018.02.041.

Md. M. Islam, A. Rahaman, and Md. R. Islam, "Development of Smart Healthcare Monitoring System in IoT Environment," SN Comput. Sci., vol. 1, No. 3, p. 185, May 2020, doi: 10.1007/s42979-020-00195-y.

* cited by examiner

SYSTEMS AND METHODS OF A MEDICAL DEVICE AND ENVIRONMENTAL CONNECTIVITY HUB

CROSS-REFERENCE TO RELATED APPLICATIONS

This application claims priority to and the benefit of U.S. Provisional Patent Application No. 63/572,012, filed Mar. 29, 2024, and U.S. Provisional Patent Application No. 63/573,306, filed Apr. 2, 2024, the contents of all of which are hereby incorporated by reference herein for all purposes.

TECHNICAL FIELD

Embodiments relate generally to a remote patient monitoring platform, and more particularly to a system that includes an Internet of Things (IoT) gateway that interfaces with medical devices, collects clinically-relevant information related to the environment and the patient condition, and connects to long-range networks to telemeter data to a cloud system.

BACKGROUND

Remote patient monitoring (RPM) is an area of increasing interest within the healthcare industry for its potential to overcome expected clinician shortages, improve patient outcomes, and decrease costs. The rapid increase of connected patients and expansion of internet availability and the simultaneous pressures on the healthcare system imposed by the COVID-19 pandemic resulted in growing support for technical solutions such as telemedicine and RPM to improve and support healthcare services.

SUMMARY

A system embodiment may include: an Internet of Things (IoT) secured gateway; a user interface comprising an interactivity tool; an environmental monitoring device configured to collect environmental data; a set of sensors configured to collect biological signals; a secure encrypted local database; and a medical hub device comprising a processor and addressable memory. In one embodiment, the system may be configured to: collect, via the set of sensors, biological signals related to patient status, where the biological signals may be collected on a continual basis; collect, via the environmental monitoring device, environmental data associated with patient environment and used for monitoring patient status, where the environmental data may be collected on a continual basis; store, locally via the secure encrypted local database, the collected biological signals and the collected environmental data spanning over a period of time; detect, by the processor, an abnormality in the collected biological signals based on comparing the collected biological signals of a current reading versus the locally stored biological signals representing a prior reading, where the abnormality detection may be executed for biological signals collected by all the sensors in the set of sensors; increase, by the processor, measurement frequency of the biological signals by the set of sensors based on the detected abnormality to determine whether the detected abnormality of the collected biological signal sensor reading with the increased frequency measurements may be consistent across sequentially collected biological signals; detect, by the processor, an error in the collected biological signals of the current reading with the increased frequency measurements based on comparing collected biological signals of an alternate sensor of the set of sensors versus locally stored biological signals representing a prior reading by the alternate sensor of the set of sensors, thereby detection of an abnormality by the alternate sensor indicates that the detected abnormality may be due to a sensor error; determine, by the processor, whether the detected error in the collected biological signals of the current reading may be due to environmental factors based on correlating the collected environmental data with the collected biological signal; correct, by the processor, the determined error in the collected biological signals by prioritizing the detected abnormality based on the correlated collected biological signals and the collected environmental data; and transmit, via the IoT secured gateway, the error corrected collected biological signals as encrypted data over a secure connection to a cloud system.

In one embodiment, the system may further be comprising a dedicated neural network accelerator chip for on-board analysis, where data points from the collected data including at least one of the biological signals and the environmental data may be extracted and only such data points may be stored wherein other identifiable patient information may be discarded. In one embodiment, values of the extracted data point may be non-linear transformations of the collected data, and therefore an original recording of the collected biological signals cannot be reconstructed from these values. In one embodiment, the dedicated neural network accelerator hardware allows the collecting and monitoring to be always on without impacting privacy.

In one embodiment, the environmental monitoring device may comprise at least one of: a particulate matter sensor, an environmental sensor, an air quality sensor, and an ambient light sensor, where the particulate matter sensor may be configured to use optical technology to detect particulate matter; the environmental sensor may be configured to measure at least one of temperature, humidity, and pressure; the air quality sensor may be configured to measure at least one of volatile organic compounds (VOCs), volatile sulfur compounds (VSCs), carbon monoxide (ACO), and hydrogen; the ambient light sensor may include a set of photodiodes in a single package configured to measure ambient light levels.

In one embodiment, the system may further be comprising a microphone array, where the microphone array may be configured to monitor coughing frequency and cough characteristics. Additionally, in order to remove privacy risks, data points including at least one of cough counts, cough features, and noise levels may be extracted on the medical hub device, and only those extracted data points may be stored and telemetered while the full audio recordings from the microphone array may be discarded.

In one embodiment, the system may be further configured to: transmit, via the user interface, a message to indicate that a sensor error has been detected based on a determination that the detected abnormality is caused by a sensor error. That is, the system may notify, via the user interface, a patient in real-time without waiting for roundtrip transmission time for communication to be transmitted to a clinical team, thereby avoid unnecessary bidirectional communication between the medical hub device and the cloud system.

In one embodiment, an error is detected if measurement data of the collected biological signals may be outside of bounds set by a clinical team. In one embodiment, if the system is not able to perform error correction, then the system may be configured to: transmit a notification to a patient to be notified in real-time from the medical hub device rather than waiting for round trip transit time for the medical hub device to communicate the measurement data to the clinical team via the cloud system. In one embodiment, no identifiable patient information is stored locally in the secure encrypted local database and all data may be tagged using randomly generated unique patient IDs for remote patient monitoring thereby avoiding unnecessary bidirectional communication between the system and the cloud system.

A device embodiment of the medical hub device may comprise: a processor and addressable memory, the device configured to: receive, from a set of sensors, collected biological signals related to patient status, where the biological signals may be collected on a continual basis; receive, from an environmental monitoring device, collected environmental data associated with patient environment and used for monitoring patient status, where the environmental data may be collected on a continual basis; store, locally via a secure encrypted local database, the collected biological signals and the collected environmental data spanning over a period of time; detect, by the processor, an abnormality in the collected biological signals based on comparing the collected biological signals of a current reading versus the locally stored biological signals representing a prior reading, where the abnormality detection may be executed for biological signals collected by all the sensors in the set of sensors; increase, by the processor, measurement frequency of the biological signals by the set of sensors based on the detected abnormality to determine whether the detected abnormality of the collected biological signal sensor reading with the increased frequency measurements may be consistent across sequentially collected biological signals; detect, by the processor, an error in the collected biological signals of the current reading with the increased frequency measurements based on comparing collected biological signals of an alternate sensor of the set of sensors versus locally stored biological signals representing a prior reading by the alternate sensor of the set of sensors, thereby detection of an abnormality by the alternate sensor indicates that the detected abnormality may be due to a sensor error; determine, by the processor, whether the detected error in the collected biological signals of the current reading may be due to environmental factors based on correlating the collected environmental data with the collected biological signal; correct, by the processor, the determined error in the collected biological signals by prioritizing the detected abnormality based on the correlated collected biological signals and the collected environmental data; and transmit, via an Internet of Things (IoT) secured gateway, the error corrected collected biological signals as encrypted data over a secure connection to a cloud system.

A method embodiment may comprise the steps of: collecting, via a set of sensors, biological signals related to patient status, where the biological signals may be collected on a continual basis; collecting, via an environmental monitoring device, environmental data associated with patient environment and used for monitoring patient status, where the environmental data may be collected on a continual basis; storing, locally via a secure encrypted local database, the collected biological signals and the collected environmental data spanning over a period of time; detecting, by a medical hub device, an abnormality in the collected biological signals based on comparing the collected biological signals of a current reading versus the locally stored biological signals representing a prior reading, where the abnormality detection may be executed for biological signals collected by all the sensors in the set of sensors; increasing, by the device, measurement frequency of the biological signals by the set of sensors based on the detected abnormality to determine whether the detected abnormality of the collected biological signal sensor reading with the increased frequency measurements may be consistent across sequentially collected biological signals; detecting, by the device, an error in the collected biological signals of the current reading with the increased frequency measurements based on comparing collected biological signals of an alternate sensor of the set of sensors versus locally stored biological signals representing a prior reading by the alternate sensor of the set of sensors, thereby detection of an abnormality by the alternate sensor indicates that the detected abnormality may be due to a sensor error; determining, by the device, whether the detected error in the collected biological signals of the current reading may be due to environmental factors based on correlating the collected environmental data with the collected biological signal; correcting, by the device, the determined error in the collected biological signals by prioritizing the detected abnormality based on the correlated collected biological signals and the collected environmental data; and transmitting, by the device, the error corrected collected biological signals as encrypted data over a secure connection to a cloud system.

BRIEF DESCRIPTION OF THE DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which.

DETAILED DESCRIPTION

Figure 1:
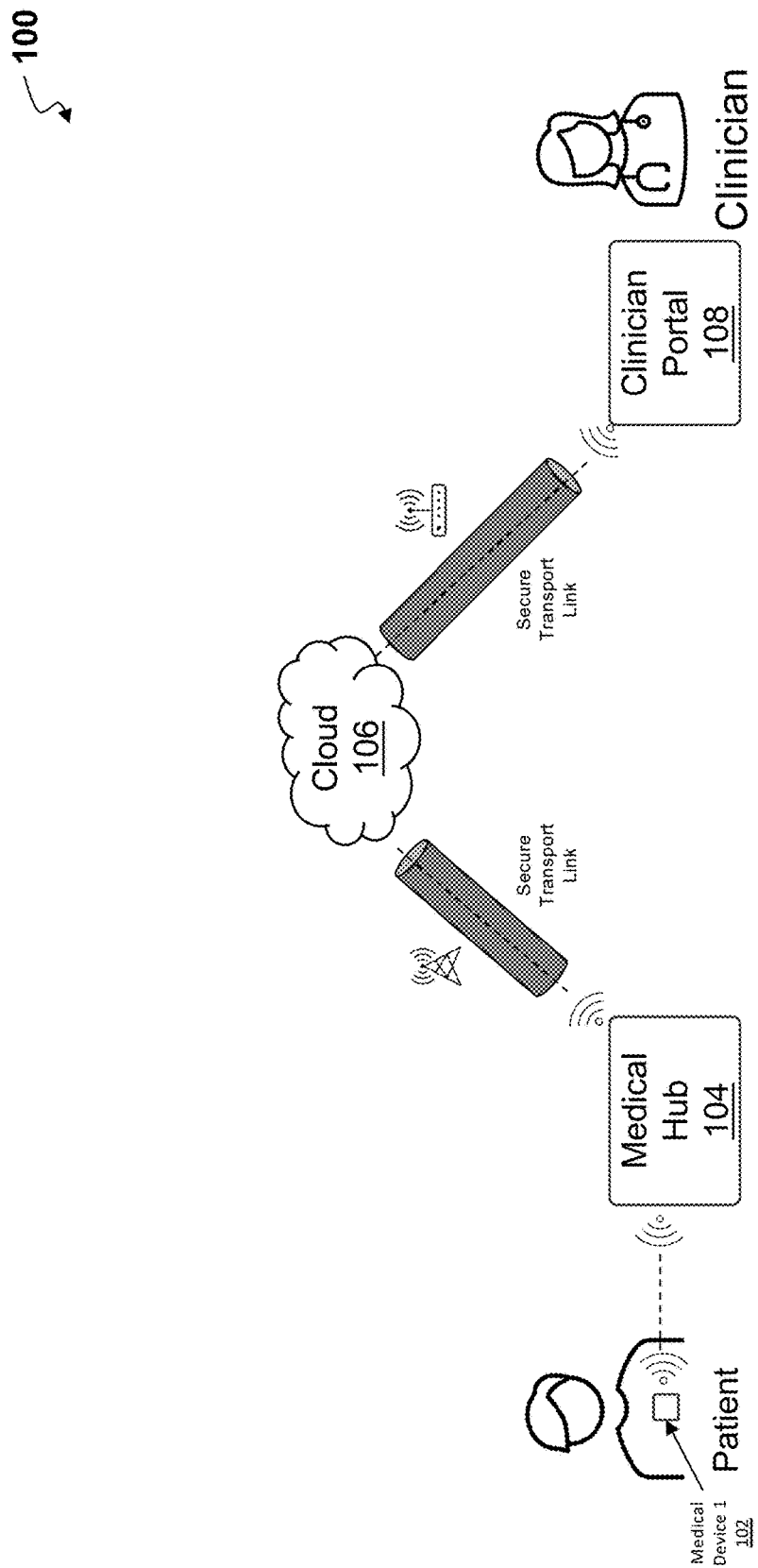
FIG. 1 schematically depicts a high-level block diagram of a disclosed system and system architecture, according to one embodiment.

Medical wearables have been introduced and adopted over the last few years to solve the issues associated with patient compliance and discrete data points. Wearables take many forms, including versions worn on the wrist, arm, and chest, and are able to take more continuous measurements of vital signs. The disclosed embodiments provide systems and devices configured to gather, for example, all five key vital signs for a patient-pulse rate, respiratory rate, oxygen saturation, temperature, blood pressure-resulting in minimizing interactions needed by the patient to remember to take measurements and increasing risk of patient drop out.

Additionally, high-quality acoustic monitoring in a wearable device is disclosed for use in continuous healthcare monitoring. Sounds from the body may be captured noninvasively, and specific spectral and temporal features that are linked to health conditions may be utilized for monitoring. The disclosed embodiments of the multi-modal wearable sensor and system may be paired with or configured to execute machine learning algorithms, thereby able to provide interpretability and diagnosis of these sounds to make significant impacts on health outcomes, as, for example, acoustic features have been linked to heart failure hemodynamics, Chronic Obstructive Pulmonary Disease (COPD) severity, and airway obstruction level.

In a remote patient monitoring (RPM) program, a patient's clinical monitoring moves from periodic to continuous sampling. Key vitals may be monitored on a more regular basis, e.g., daily, or even hourly, at home by the patient or with help from a relative, instead of moving to a health care unit where a nurse collects measurements more sparsely. With the evolution of health conditions being better monitored, the occurrence of other conditions may be predicted based on a more continuous sampling in natural contexts. These systems then allow for real-time alerting and communication channels to mitigate worsening symptoms or other risks. When used in these contexts, RPM solutions have been shown to improve the efficiency of diagnosis, the prevention of risk situations, the effectiveness of treatments, and the promotion of good health. Clinical results largely support the use of RPM solutions, as they contribute to the expansion of access to quality healthcare while also allowing for more autonomy and quality of life for patients. Therefore, connected devices in remote patient monitoring may be utilized as described further herein.

Existing solutions have created an over-reliance on smartphones and mobile platforms. The requirement to use a mobile application to interface with connected devices and telemeter data to the cloud means that segments of patient populations are not able to fully benefit from these solutions. Patients may lack the technical literacy to engage fully with smartphones, lack the financial means to access a smartphone or wireless plans, or may have disabilities that preclude them from being able to use a smartphone. Paradoxically, patients that fall in these categories—such as pediatric, elderly, rural, economically disadvantaged, or disabled patients—are statistically more likely to have increased healthcare demand and would most benefit from participating in remote patient monitoring programs that reduce the need for inpatient visits.

Manufacturers grapple with the challenges related to the wireless technology used to telemeter data. In many cases, the same patients as described above may have difficulties having to manually set up a connection to their home Wi-Fi. Many remote patient monitoring companies have begun to rely on cellular connectivity to transmit data. Service providers rely on devices that each individually connect with a cellular network.

The disclosed system embodiments increase access to RPM solutions by reducing failure points when trying to capture data. Thereby, not relying on a single cellular provider allows for control of outages, poor coverage, or cell tower downtime. The disclosed RPM programs are not a reactive measure where a patient is enrolled in a program after an acute event or worsening symptoms. That is, RPM solutions provided herein have the ability to capture data in natural contexts, measure, and understand how these natural contexts directly impact patient health for preventative intervention. For example, exposure to high levels of humidity, VOCs, or PM2.5 in the air is directly related to the living environment, including ventilation, cleaning supplies, and gas stoves, and can have detrimental health effects for patients with chronic respiratory and cardiovascular diseases. Proper environment measurement-symptom correlations and subsequent education for patients on the management of these environmental factors could significantly improve patient health outcomes and therefore, one focus of the present systems, devices, and methods of a medical device and environmental connectivity hub.

The present embodiments disclose a hub, used for linking multiple computers and devices together, that is designed to be a fully integrated solution for remote patient monitoring, where the hub includes a smart Internet of Things (IoT) gateway, a user interface having an integrated display and interactivity tool with input/output display, and environmental monitoring device. In one embodiment, the IoT gateway may be configured to provide IoT security in the form of edge-based security via incorporating integrated security functionality that sits between IoT devices and the public Internet data minimization. The IoT gateway may also be configured to execute filtering of collected data produced by IoT devices before sending the data out over the Internet, helping to reduce both the volume of data sent and the amount of sensitive information that may be leaked in network communications or via compromised cloud-based servers.

The disclosed hub may be configured to provide connectivity for patients who, for example, may not have regular access to internet-enabled smartphones, a stable home internet connection, or any home internet connection. The hub provides a user interface for patients undergoing remote monitoring programs and a tool, as an interactivity tool, to conduct remote visits with care teams over voice and video calls. The hub may be a medical hub and may be configured to communicate with Bluetooth-enabled medical devices used by the patient, for example, over up to approximately 30 m away in standard home environments and uses a plurality of wireless technologies to transmit the data to the cloud, where all the data may be accessed in real-time by the clinical team through a web-based portal.

FIG. 1 depicts a high-level block diagram of the disclosed system 100 and system architecture showing a patient using a medical device 102 where, for example, Medical Device 1, may transmit data to the medical hub 104, and the medical hub 104 in turn may communicate with the cloud 106 via a secure transport link; the cloud 106 may then transmit the data via another secure transport link to a clinician portal 108 where a clinician has the ability to view the data. In one embodiment, the medical device 102 may be configured to collect data that are in the form of biological signals (also referred to as biosignals), which reference space, time, or space-time records of a biological event such as a beating heart or a contracting muscle. That is, the electrical, chemical, and mechanical activity that occurs during these biological events often produces signals that may be measured and analyzed. Biological signals may be detected via electrodes or transducers that are configured to continually measure and monitor such signals.

Figure 2:
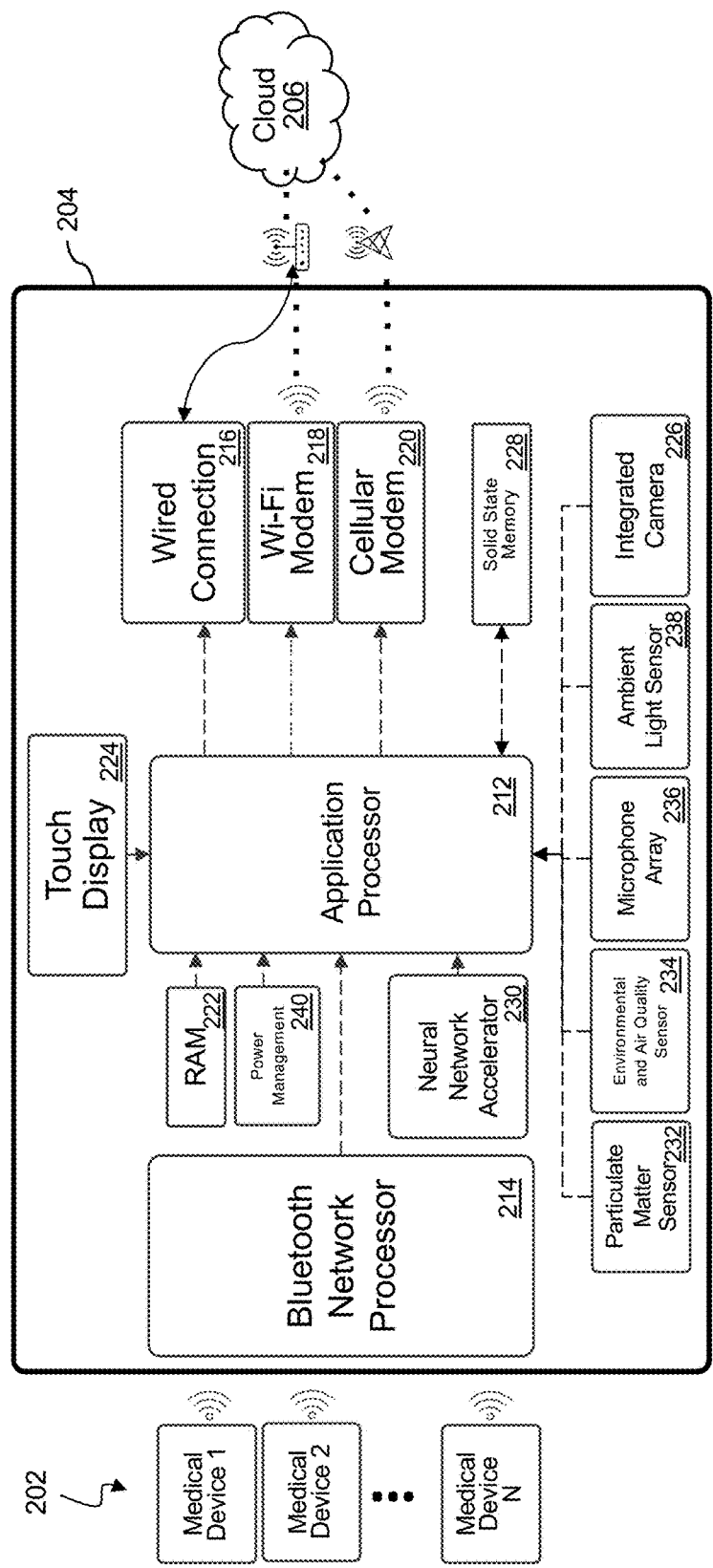
FIG. 2 depicts a high-level block diagram of a hardware architecture of the disclosed system, according to one embodiment.

FIG. 2 depicts a high-level block diagram of a hardware architecture of the disclosed system. Referring to FIG. 2, the disclosed system 200 may include a plurality of medical devices 202, Medical Device 1, Medical Device 2, . . . , Medical Device N, a medical hub 204, and a cloud 206. The medical hub 204 may comprise two processor cores including Application Processor 212 and Bluetooth Network Processor 214, a wired connection 216, two wireless modems including a Wi-Fi modem 218 and a cellular modem 220, onboard memory such as RAM 222, an integrated display such as a touch display 224, an integrated camera 226, a set of sensors, onboard storage such as a solid state memory or addressable memory 228, and an optional neural network accelerator chip 230. The set of sensors may include a particulate matter sensor 232, an environmental and air quality sensor 234, a microphone array 236, an ambient light sensor 238, etc. The hub may also comprise a power management module 240.

Figure 3:
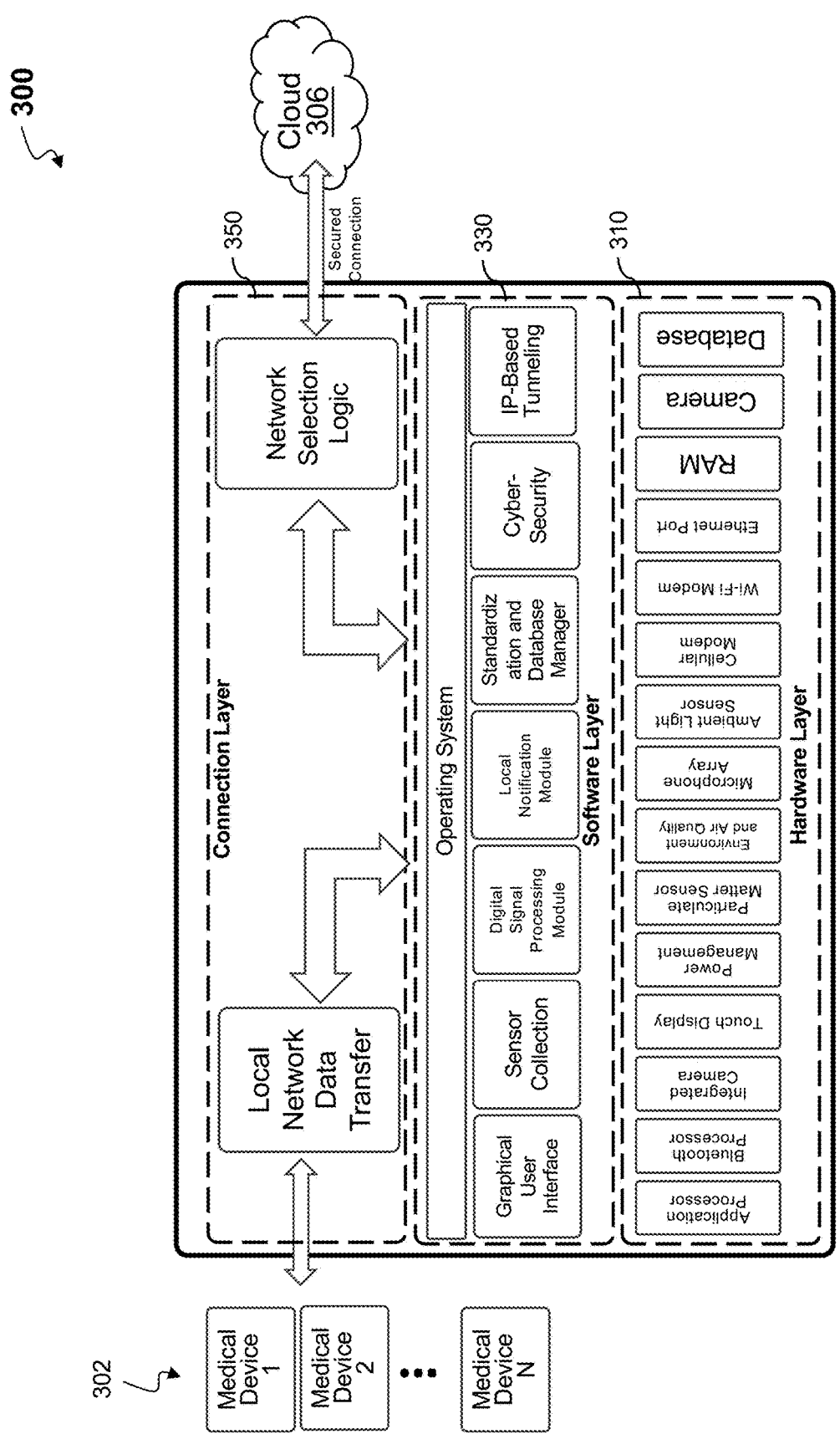
FIG. 3 depicts a high-level block diagram of a hub configuration, according to one embodiment.

FIG. 3 depicts a high-level block diagram of a hub configuration 300, according to one embodiment. The hub configuration 300 may include a hardware layer 310 as shown in FIG. 2, a software layer 330, and a connection layer 350, respectively. Referring to FIG. 3, the Application Processor may be the primary processing unit that controls a graphical user interface, sensor data collection, a digital signal processing module, a local notification module, data transfer, Bluetooth and internet connectivity management, onboard processing of data, database management and implementation of all cybersecurity protocols, IP-based tunneling, etc. The Bluetooth Network Processor may be responsible for communicating with the medical devices 302 and receiving data over Bluetooth connections. The onboard storage, e.g., local database, may be used to retain configuration and device information and act as a secure local database to retain backups for recently collected data. The hub configuration 300 may have an integrated display, such as a touch display, which may be used by the patient to interact with the system when needed and remove any dependency on patient smartphones or tablets. The integrated display may also be used when conducting video calls with the care team. The optional neural network accelerator chip may allow for complex deep learning analysis to be run on the hub without requiring a connection to the cloud.

The integrated display, camera, and microphone array on the system, described in FIGS. 2 and 3, may be used to help manage care throughout the RPM program. The integrated display may be configured to remind patients when to take measurements and aid patients through the process of applying a medical device and taking a measurement. Other notifications and reminders may be able to be provided to patients, such as when to take certain pills, communications from their clinical team, or notifications and alerts from the cloud system regarding abnormalities. The integrated display, such as a touch display, may also allow patient inputs, to select items or to complete questionnaires or patient-reported outcome surveys. This type of qualitative data may help contextualize the quantitative data that is being collected by the medical devices. Clinical teams may be able to send content for patients to review, which may be done on the screen of the hub. For example, if the patient is part of a physical therapy program, the hub may display a series of exercises for the patient to complete and then collect clinical data when the exercises are being completed. Finally, the integrated display may operate with the camera and the microphone array in order to facilitate voice or video calls with clinical teams. These tools may be frequently used during the RPM program to track progress, assess symptoms, or support adherence; the integration of these tools within the hub may remove reliance on home phones and the internet or smartphones to complete these virtual visits.

Several features may be implemented to limit the connection bandwidth needed by patients to undergo routine RPM programs. First, patients may frequently need to access recent data readings for self-monitoring and need to be fetched from the cloud to be viewed. In order to avoid unnecessary bidirectional communication between the hub and the cloud system, recent data, for example, from the last 30 days (or a configurable amount between approximately 5 to 180 days), may be stored locally in the hub's secure encrypted local database. The local database may have a configurable memory size, for example, up to 64 GB. Data larger than a single data packet (e.g., 2 KB) and being transmitted via a standard for IoT Messaging, may be backed up in the local database. In one embodiment, data may be stored in both the cloud and locally, for redundancy. Since the data may be stored in non-editable tables in both the cloud and the local database, synchronization of the values is not required. In one embodiment, the local storage may happen regardless of the current speed/latency of the connection because the current values may not be indicative of future values when the data may be needed/retrieved. The storage of the data may follow standard medical data privacy and security protocols. This feature may be configured to be executed directly in gateways (e.g., secure gateway) or other RPM solutions and may reduce bandwidth requirements for shuttling data files between the hub and cloud when connectivity is challenging.

Additionally, the hub may allow for onboard processing of data readings, frequently referred to as 'computing at the edge.' Edge computing may allow for the management of bandwidth requirements over limited connections. By processing and managing health data locally, remote services may be executed on the local devices and moved nearer to the user, thereby reducing risk associated with data loss, connectivity loss, or time delays. Daily, weekly, and monthly averages of parameters stored in the local database may be calculated and presented to patients for monitoring of their vitals long term. In one embodiment, complex analysis may also be conducted via the on-board processing of data readings. For example, the output for an electrocardiogram (ECG) reading is a time series waveform. In this case, the processing may be done to transform these large time series waveforms into singular values, including pulse rate, heart rate variability, and abnormalities like arrhythmia detection. In connectivity-poor settings, these calculations may be done in the hub, while a single reading from one or more sensors, a single data packet, and/or a set of abnormal segments may be transmitted to the cloud at lower connectivity speeds and bandwidth requirements than the full-time series files. Further, if these measurements are outside of bounds set by the clinical team, the patient may be notified in real-time from the hub rather than waiting for the roundtrip transit time for the hub to communicate the data to the clinical team (via the clinician portal) and then back to the hub.

In one embodiment for example, for patients that are being monitored for abnormalities after being discharged from the hospital, when an abnormality is detected—whether absolute (e.g., presence of cough) or relative (e.g., cardiac output decreases relative to baseline at discharge)—the system may go through a multi-step process to attempt to contextualize the abnormality prior to alerting the care team. In these embodiments, if any abnormality is detected, the system may be configured to increase the frequency of measurements to see if the abnormality is consistent across sequential recordings. The system may then attempt to determine if there was an error, error detection, in the sensor reading signal that resulted in the abnormality by checking other sensor signals. For example, it is unlikely that oxygen saturation is low without either heart rate or breathing rate being high or breathing effort being high. Additionally, the system may also be configured to determine if the abnormality could likely be caused by environmental conditions, via error contextualization. In the example of the cough from above, the system may be configured to determine if it could be caused by low air quality, high volatile organic compounds, or high particulate matter at the patient's home, etc. Finally, the system may be configured to prioritize the abnormality, via an error correction process, into low, medium, or high severity based on the context above and send an alert to the patient's care team, where the system is configured to transmit the error corrected data.

Accordingly, the system is configured to detect an abnormality, determiner if the abnormality is based on sensor error, if determined not to be a sensor error, then use environmental data to determine a correlation between the sensor readings and the environmental factors (via environmental data being collected) and perform an error correction by using alternate sensor and reasons for the abnormality. Thereby the system, via the medical hub and set of sensors along with environmental data, is configured to determine or reasonably predict the reason behind the abnormality before contacting the patient care team. If the system determines that there isn't a sufficient explanation for the abnormality, the system may then transmit the information to a cloud environment to process the data and contact the care team if the abnormality is not explained reasonably. The purpose of the system is to eliminate or reduce false alerts and create a self-sufficient echo system for patients before alerting the patient care team. That is, in the example where the system is configured to prioritize the abnormality into low, medium, or high severity, each prioritized severity may trigger a different response. In this embodiment, a low severity may indicate that the patient care team does not need to be informed at all or informed right away; a medium severity may indicate that the patient care team needs to be informed but without it being considered an emergency; and the high severity may indicate that the patient care team needs to be informed immediately since this may be an emergency situation with the patient. As described herein, all these settings, triggers, and determinations may be customized to the patient by setting individualized thresholds. Alternatively, the machine learning aspect of the algorithm may dynamically determine such settings, triggers, and determinations based on accumulated data from other patients across the platform and used as training data in machine learning train the model.

In one embodiment, the hub may be configured to perform error detection on the collected data, where, for example, an error in the signal may indicate that the sensor was not able to accurately read the data or function according to specification. The hub may be configured to perform error correction in this scenario, for example, the wearable system may have six sensing modalities, where two or more of the sensors may be configured to collect biosignals associated with or relevant to heart rate detection. One embodiment may use a Photoplethysmography (PPG) which is an optical technique used to detect volumetric changes in blood in peripheral circulation via making measurements at the surface of the skin. If the heart rate from PPG is abnormal, in one embodiment, the heart rate data may be checked against other modalities (e.g., ECG, auscultation) via sensors configured to be listening to the sounds produced within the body to ensure correct values are being recorded/reported. Additionally, the error correction may occur by the user device (or in the case of the wearable device) being configured to take the measurement again, either via the same sensor or a set of alternative sensors that are configured to make such measurements. If the values remain consistent, meaning that data continues to be abnormal, then in one embodiment, the notification may be transmitted to the cloud and the patient care team, e.g., a clinician.

In one embodiment, via local execution by a processor running on the hub, the hub may detect abnormality in the received data from the set of sensors by continuously comparing current sensor data readings against prior locally stored sensor data readings previously received and stored on the hub from the same sensor. That is, the hub processor may be configured to execute abnormality detection by continuously collecting and comparing data, the data including biological signals received from one of the set of sensors against prior signal readings, locally stored, from the same sensor of the set of sensors. In one embodiment, if the current sensor data readings vary by a predetermined threshold from the prior sensor data readings, the processor may then be configured to trigger additional processing based on the detected abnormality in the received data from the sensors.

In the embodiment where an abnormality is detected, the processor may then be configured to determine whether an error has occurred in the sensor reading, causing the abnormality. That is, an error detection aspect of the process determines whether the abnormality is due to the patient who is being monitored or due to an incorrect reading from the set of sensors, for example, a malfunction in the sensor. That is, if the abnormality is one attributed to the patient's status, then it needs to be transmitted to the clinical team. To determine the cause of the abnormality, in these embodiments, the processor may be configured to determine whether the detected error is caused by the sensor via checking one of the other sensors in the set of sensors for abnormal data readings. In the scenario where an alternative sensor of the set of sensors provides a set of substitute data readings, for example, heart rate, for the same time period where the original sensor transmitted an abnormal reading, the hub may perform an error correction and determine that the abnormality was due to the sensor malfunctioning and not the patient having experienced a health concern.

In an embodiment where the alternate sensor of the set of sensors has transmitted an abnormal data reading as well, the processor, now having received multiple abnormal signals, may attribute the abnormality to the patient's health and proceed to check whether environmental factors may have caused the abnormality in the data readings. That is, via the environmental sensors, the hub may determine whether the patient's environment may have contributed to the abnormal data reading by checking the environmental sensors and looking for any correlations, for example, coupling the biological data with environmental data, to determine if there is a reason for the abnormality. In one embodiment, the environmental sensor readings may be used to contextualize the abnormal biological data received from the patient and thereby infer, learn, and extrapolate potential causes for the abnormality. In one embodiment, the hub may be configured to transmit the abnormal data readings along with the environmental sensor data without any further processing to aid the patient care team.

In one embodiment, if determined that the detected abnormality in the received data from the sensors is not due to sensor error, via the error correction, and not due to environmental factors, via the environmental sensors, the hub may transmit the associated readings to the cloud since locally all processing has been executed. In one optional embodiment, at the cloud and before informing the clinician portal and the clinician, the cloud system may compare the received signal data readings with previously collected data readings of other similar patients. This way, another layer is added to catch any abnormal readings that may otherwise be considered normal. That is, the system aims to exhaust all the resources at the hub initially, then at the cloud, and when necessary, contact the clinician team. Additionally, at both the local hub processing and cloud system, clinical thresholds may be used to determine whether the abnormality detected is considered an abnormal reading from the patient having to do with their health.

Optionally, the Application Processor may also interface with a purpose-built secondary neural network accelerator chip on board the hub in order to conduct more complex machine learning classification tasks on the edge. The secondary neural accelerator applies neural processing for multiple application types by running deep neural networks (DNNs) natively, including convolutional neural networks, recurrent neural networks, and fully connected networks. The parameters of the neural networks (e.g., weights and biases) contained within the neural network accelerator are software configurable and may be updated from the cloud system, similar to 'software updates', as improved baseline models are available. These baseline models may be loaded into the neural network accelerator and then fine-tuned using the local data contained within the hub.

Onboard processing of data may also allow for the maintenance of privacy for certain measurements taken by the hub. For example, audio recordings may be taken by the onboard microphone array (which may be part of the environmental monitoring device) to detect coughing and monitor levels of environmental noise. These audio recordings may be considered sensitive recordings of private spaces, and extreme caution should be taken when handling such data. In order to remove privacy risks, cough counts, cough features, and noise levels may be extracted on the hub, and only those extracted data points may be stored and telemetered while the full audio recordings are discarded. These extracted values may be non-linear transformations, meaning that the original audio recording cannot be reconstructed from these values. The dedicated neural network accelerator hardware may allow this monitoring to be always on without impacting privacy.

In the disclosed embodiments, signal processing may be configured to be executed in the Application Processor of the system. The Application Processor may have a dedicated Digital Signal Processor (DSP) module for performing these and other mathematical functions. That is, the DSP module may be used to take real-world signals like voice, audio, video, temperature, pressure, or position that have been digitized and then mathematically manipulate them. The disclosed DSP module may be designed for performing mathematical functions like "add", "subtract", "multiply" and "divide" very quickly.

In one embodiment of the disclosed systems, the hub may provide wireless connectivity and use multiple redundant connectivity options with fail-safes implemented for data management and streaming to ensure total reliability. The hub's primary method of communication may be through cellular connectivity, with an optional Wi-Fi connection to connect to the patient's home Wi-Fi, an optional ethernet port for a wired connection to an internet modem, and onboard storage to store data during gaps in connectivity. If patients have home internet and are comfortable with the task of setting up the system on their home internet, they may be able to do so on the system. Otherwise, the hub will default to the use of cellular connectivity, reducing the burden on patients and allowing for 'out-of-the-box' functionality.

Figure 4:
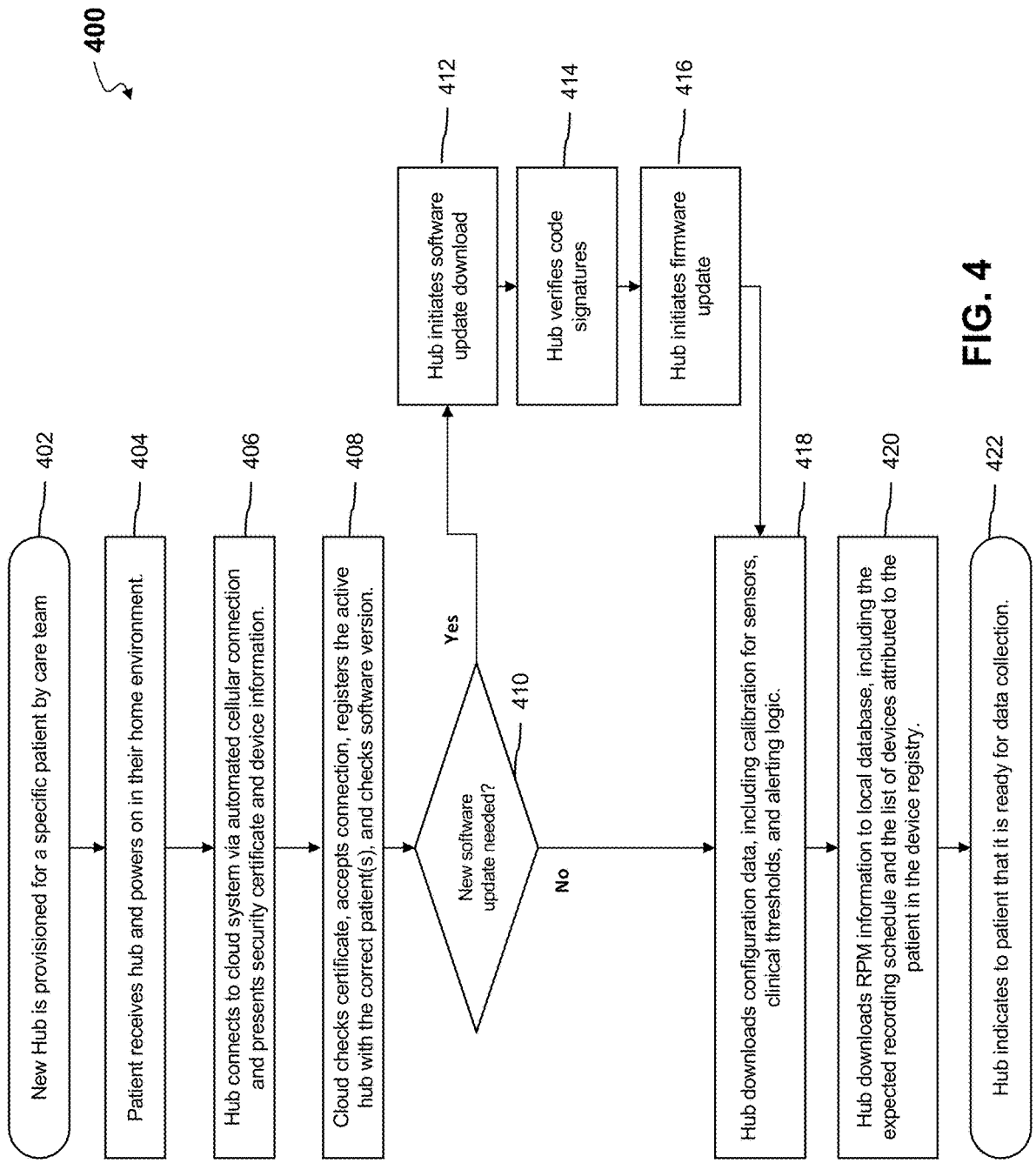
FIG. 4 depicts a flow diagram of a hub initiation process and automated device configuration at startup, according to one embodiment.

FIG. 4 depicts a flow diagram of a hub initiation process using automated device configuration at startup. The process 400 of disclosed embodiments may be configured to provide 'out-of-the-box' functionality to remove any friction in setting up patients on Remote Patient Monitoring (RPM) programs. The patient may be instructed to simply plug in the hub to power on. Wireless connectivity, discussed below, may initialize automatically and begin setup and configuration automatically. Referring to FIG. 4, initially, a new hub may be provisioned for a specific patient (step 402). When the patient is assigned the new hub, the hub unique identifier (UID) may be registered to the patient in the cloud system before being sent to the patient. When the patient receives the hub, the patient may be instructed to simply plug in the hub to power on the hub in their home environment (step 404). When the patient receives the hub and powers it on, the hub may be automatically connected to the internet. The hub may then communicate with the cloud to establish secure connections, via automated cellular connection and present a security certificate and device information (step 406). The cloud may check the certificate, accept the connection, register the active hub with the correct patient(s), and check for software updates (step 408). That is, the cloud-based computing device may determine whether a new software update is needed (step 410). If the software update is needed, the hub may initiate a software update download (step 412). The hub may verify code signatures (step 414) and initiate firmware updates (step 416). When the software update is completed, or the software update is not needed, the hub may download configuration data, including calibration for sensors, clinical thresholds, and alerting logic (step 418). The hub may also set up patient information or download RPM information to the local database, including the expected recording schedule and the list of devices that are attributed to the patient in the device registry (step 420). The hub may then be configured to indicate to the patient that it is ready for data collection and use (step 422). In one embodiment, this configuration data may be regularly synced with the cloud to ensure up-to-date information. By handling all configurations remotely and automatically, patients may be seamlessly set up on RPM programs.

Figure 5:
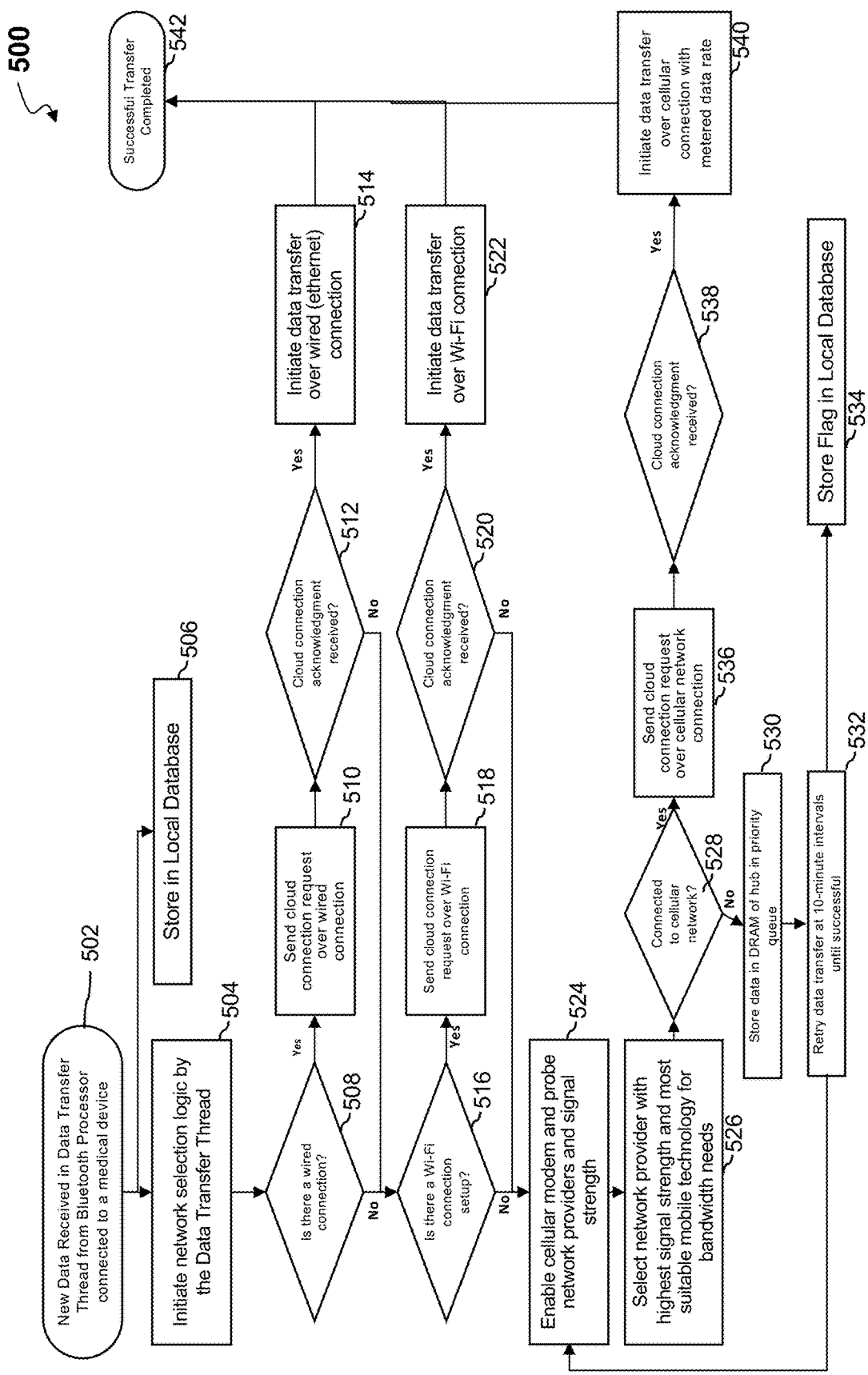
FIG. 5 depicts a flow diagram of a data transfer process and network selection logic, according to one embodiment.

FIG. 5 depicts a flow diagram of a data transfer process using network selection logic where the connection, via cellular technology, is determined through an onboard network selection logic that is fundamentally unique in the field of medical device gateways. Referring to FIG. 5 for the process 500 of disclosed embodiments, when new data is received in a data transfer thread from the Bluetooth Processor connected to the medical device (step 502), the data transfer thread may initiate network selection logic (step 504), and at the same time, the new data may be stored in the local database (step 506). The network selection logic may be configured to prioritize connecting to the wired connection, followed by the Wi-Fi connection. The network selection logic may determine whether there is a wired connection, for example, ethernet (step 508). If the connection is a wired connection, the system may send a cloud connection request over the wired connection (step 510). If the cloud connection acknowledgment is received (step 512), data transfer may be initiated over the wired connection, (step 514), and the successful data transfer may be completed (step 542). On the other hand, if the cloud connection acknowledgment is not received (step 512), the network selection logic may determine whether the connection is a wireless connection, for example, Wi-Fi (step 516). If the connection is via a Wi-Fi connection, the system may send a cloud connection request over the Wi-Fi connection (step 518). If the cloud connection acknowledgment is received (step 520), data transfer may be initiated over the Wi-Fi connection (step 522), and the successful data transfer may be completed (step 542). If the Wi-Fi connection is unavailable, the system may enable a cellular modem and probe network providers and signal strength (step 524) and select the network provider with the highest signal strength and most suitable mobile technology for bandwidth needs (step 526).

Figure 6:
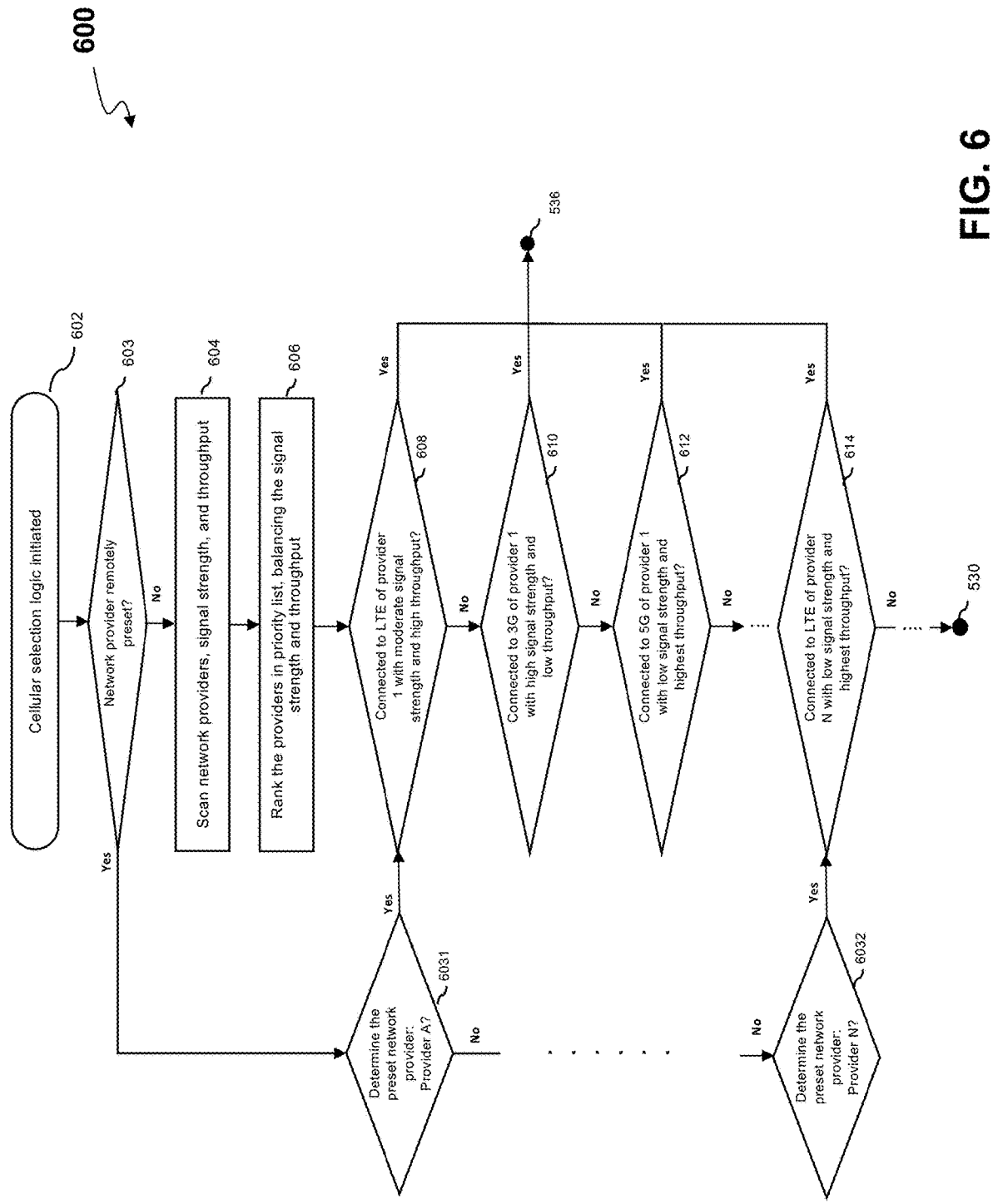
FIG. 6 depicts a flow diagram of a cellular selection logic of the network selection logic, according to one embodiment.

FIG. 6 depicts a flow diagram of a cellular selection logic of the network selection logic. Specifically, referring to FIG. 6, the system may employ cellular selection logic 600 to automatically select key attributes, such as the network provider, the mobile technology (5G, 4G, or 3G), and the priority of services that would optimize the cellular connection to ensure the most reliable connection for the patient's geographic location and connection requirements (step 602). The ability to connect to any of the network carriers, such as three major network carriers and doing so through software-only techniques are disclosed herein. In the embodiments, eSIMs may be leveraged such that a single SIM card and a single modem may be used for the full set of cellular providers.

The eSIMs may allow for the credentials for a mobile network to be remotely programmed. To select the provider to credential for and connect to, the system may scan for network providers, signal strength, and throughput level (step 604) and rank the providers in a priority list, balancing these two metrics (step 606). An example ranking would be: (1) a moderate signal strength for LTE of provider A (high throughput), (2) a high signal strength for 3G of provider A (low throughput), (3) a low signal strength for 5G of provider A (highest throughput), . . . , (n) a low signal strength for LTE of provider N (highest throughput), etc. If the connection at the highest priority level fails (step 608), the connection attempt will automatically move down to the next level on the priority list to maintain connectivity (steps 610, 612, 614). Additionally, the priority may be remotely set to prefer a specific provider (step 603). For example, if the provider, such as T-Mobile, is known to be more reliable in a certain geographic area, a technician can remotely set T-Mobile to always be the highest on the priority list for the first connection attempt (step 6031). Therefore, this preset network provider may eliminate the need to include multiple modems . . . or, at the minimum, multiple SIM cards . . . for each cellular provider that needs to be connected. In another example, if provider N is preset as a network provider by a technician, provider N may be highest on the priority list for the first connection attempt (step 6032). In this case, step 614 may be attempted first, and then other connection attempts, steps 608, 610, 612, and others for different providers may be subsequently attempted, unlike the order of steps 608, 610, 612, and 614 shown in FIG. 6. Thereby, the disclosed embodiments provide that individual connections via these modems may not be needed to be managed through the microcontroller. This embodiment depicts a system that does not require complex hardware architectures involving multiple cellular modems, and where the system may leverage mobile virtual networks (MVNs) such that switching between network providers and the technology may be executed via special software.

The MVNs on all three major network carriers in the United States may cover the 99.9% of Americans who live in areas with access to at least one internet service provider and are covered by at least a 3G mobile network. Additionally, satellite connectivity may be used in this system. The network selection logic may be designed such that if a connection via one network carrier fails, the system is configured to automatically switch to another network carrier with roughly only approximately 15 seconds of switching time. In current predicate systems, where multiple network options may not be employed, connectivity may be dependent on a single cellular provider which may lack coverage in that patient's particular geographic area or may be experiencing downtime during a data transfer. This methodology may also allow for the selection of multiple protocols: the use of low-level protocols like LTE-M for most data transfers, 3G for alerts, commands, and messaging, and the ability to jump up to 5G or LTE for high bandwidth tasks like audio and video calling. The network selection logic may also allow for the prioritization of real-time services, such as voice and video, when multiple data connection types are needed simultaneously.

These connectivity redundancies and the network selection logic in the hub may provide multiple fail-safes such that there will be no interruptions in the data stream from the patient to the care team. For example, if a hub is connected to a home internet that is unstable and drops out at the time of transfer, data will automatically be routed over the cellular connection. If, for example, the hub is currently using the T-Mobile cellular network and there is an outage in the network, the hub's network selection logic can automatically switch to AT&T so that there may be no interruption in the connection and data may be transmitted in real-time to the cloud. Referring to FIG. 5 again, if there is no available cellular network (step 528), and thus, there are no connections currently available through any of the connectivity options, the device may be configured to store the data in a stack in the DRAM in the hub (step 530). The system continually re-attempts to establish a connection and retry data transfer at a determined interval on a regular basis, such as approximately 10-minute intervals (step 532), and then once successful (steps 528, 536, 538), will upload all the data stored in memory such that none of the data is lost during network downtime (step 540). Accordingly, successful data transfer may be completed (step 542) when the above logic is executed. If connections are not available, the flag for the data may be stored in the local database (step 534).

In the case where connection is lost in the middle of a transmission of data, the disclosed system embodiment may be configured to attempt a reconnection on any alternative connection options and restart the transmission in full, so as to avoid any gaps in data that may have occurred at the time of the connection drop.

Figure 7:
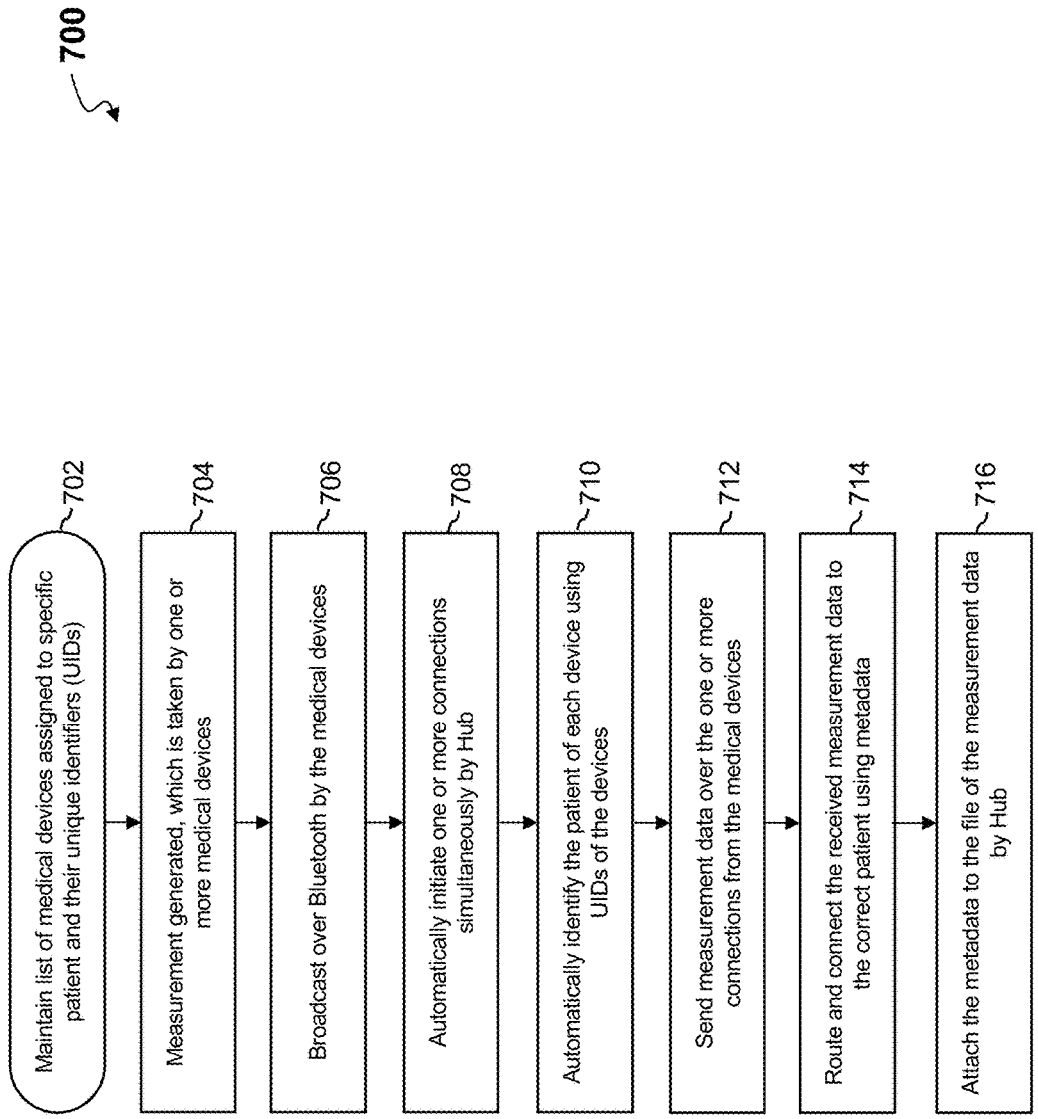
FIG. 7 depicts a flow diagram of a connection process between a hub and wireless-enabled devices via Bluetooth, according to one embodiment.

FIG. 7 depicts a device connectivity flow diagram of a process for connection between the hub and wireless-enabled devices via Bluetooth. The Bluetooth Network Processor shown in FIGS. 2 and 3 may be used for the process 700 of disclosed embodiments to connect the hub to wireless-enabled devices. Referring to FIG. 7, the Bluetooth Network Processor (see also FIG. 2) may maintain a list of the medical devices that are assigned to the patient and their unique identifiers (UIDs) (step 702). When a measurement is being taken (step 704), in one embodiment, the device may begin to broadcast over Bluetooth (step 706), and the hub automatically may initiate a connection (step 708). The medical device will then send data over this connection (step 712). When data is collected from the medical device, the metadata from the hub may allow the system to automatically route and connect the data to the patient (step 714), and then the hub may attach the metadata to the file, including UID, timestamp, and other identifying information (step 716).

In some embodiments, the system may be configured to connect to several different devices that are used to monitor multiple patients simultaneously. There may occur instances where two or more patients in the same household or living facility are under monitoring. In this instance, they may be monitored using the same hub. The hub may be configured to automatically identify which device is associated with which patient using UIDs of the devices that are stored locally in the hub configuration and in the device registry in the cloud (step 710). When data is collected from a device, the metadata from the hub may allow the system to automatically route and connect the data to the correct patient. The Bluetooth Network processor may also allow for up to four (4) simultaneous and active Bluetooth connections so that no issues arise when multiple devices are in use. In one embodiment where multiple users are signed up to use the hub, the system may use biometrics. For example, voice recognition may be used to detect which user is the one coughing. That is, cough sounds may be differentiated between patients.

Additionally, in one embodiment, the system may have the ability to turn the hub into an access point via the Wi-Fi modem through software controls. Access points are virtual routers that may create connections to a network. In this case, the hub may be configured to generate a secure local area network. If the patient does have a mobile phone and wants to use it to interact with the hub through their phone, the mobile application may automatically connect to the hub using the software-enabled access point. This feature may allow patients, who are comfortable doing so, to engage with the hub at a distance. It may also reduce vectors for security threats by creating a local network to communicate directly without opening up the system to the outside world.

Another feature of the disclosed hub embodiments may be the implementation of Environmental Monitoring with an integrated ability to collect environmental data that would inform patient status, especially in the monitoring of respiratory and cardiovascular diseases. In one embodiment, the collected environmental data may be performed on a continual basis and in real-time. The hub may measure several key environmental indicators—temperature, humidity, pressure, volatile organic compounds (VOC), air quality, fine inhalable particulate matter, ambient light, and ambient noise—each of which has been shown in the literature to correlate highly with symptoms and the exacerbation of existing symptoms in at-risk groups. That is, the disclosed system monitors natural environments for symptom correlations. By monitoring these environmental and symptom-related factors that are leading indicators for health status, the system is able to proactively manage patients and their symptoms.

Referring to FIGS. 2 and 3 again, a first sensor of a number of sensors, may be the environmental sensor configured to measure temperature, humidity, and pressure. High indoor temperatures have been shown to be associated with increased respiratory distress calls made to paramedics. When indoor relative humidity decreased from 75% to 45%, inflammatory and coagulatory indicators decreased significantly, and pulmonary function metrics (PEF, FEV1, and FVC) increased significantly.

In one embodiment, a second sensor of a number of sensors may be the air quality sensor configured to measure volatile organic compounds (VOCs), including volatile sulfur compounds (VSCs), carbon monoxide (ACO), and hydrogen. VOCs in the indoor environment are compounds that may be derived from scents, cleaning agents, pollutants, etc. that have a high vapor pressure at room temperature. VOCs in the external environment may be generally associated with the combustion of fossil fuels. Most VOCs may not be acutely toxic at low levels but may have long-term chronic health effects from elevated levels or prolonged exposure. For example, high indoor VOC levels at home are associated with nose and throat irritation, worsening asthma symptoms, and increased risk of atherosclerosis. This same sensor may generate an Index for Air Quality (IAQ) between 0 to 400, where a value of 0 is excellent, near-pure air, and values greater than 250 may be severely or extremely polluted with harmful VOCs present and possible neurotoxic effects.

In one embodiment, a third sensor of a number of sensors may be the particulate matter sensor configured to use optical technology to detect particulate matter that may be approximately 2.5 micrometers and smaller (PM2.5). Particulate matter may be a complex mixture of solid particles and liquid droplets generated from industrial sources; fuel combustion for cooking, heating, or transportation; dusting; candle burning; pollen; and bacteria and fungus. PM2.5 may have a higher incidence rate and deposition rate in the lungs than other particles, resulting in a higher degree of impact on the respiratory tract. The National Ambient Air Quality Standard (NAAQS), set by USEPA, stipulates 35 $\mu g/m^3$ and 15 $\mu g/m^3$ for 24 h and annual periods, respectively, for exposure to PM2.5. Countless studies have been published linking fine particulate matter to a decrease in cardiopulmonary function, vascular damage, and detrimental long-term effects. Oxygen saturation was reduced, and pulse rate and diastolic blood pressure increased for increases in PM2.5, temperature, and relative humidity. Self-rated health diminished with increases in PM2.5 and temperature. There was a significant reduction in pulmonary function and a rise in symptoms such as cough and sputum when COPD patients were exposed to PM2.5. The sensor may be able to monitor PM2.5 concentration and length of exposure to elevated PM2.5 relative to the NAAQS.

In one embodiment, a fourth sensor of a number of sensors may be an ambient light sensor, which may include a set of photodiodes in a single package to measure ambient light levels, which have been shown to have varying levels of impact on health. In one study of young adults, ambient light significantly raised systolic blood pressure but only had a moderate effect on diastolic blood pressure. In another study utilizing national data, overall light exposure was negatively associated with sleep duration, which could have downstream effects on cardiovascular health.

In one embodiment, a fifth sensor of a number of sensors may be a microphone array. The microphone array may serve several purposes. First, the system may monitor coughing frequency and cough characteristics, both of which are clinically meaningful. Patients with uncontrolled asthma have been shown to have higher median 24-hour cough frequency compared with partially controlled asthma and controlled asthma, similar to patients with and without acute exacerbations of COPD. Cough features have also been shown to correlate highly with lung obstruction and patient disease state relative to spirometry. Second, the microphone array may be used to monitor ambient noise levels. Studies have shown an increased risk of myocardial infarction and cardiovascular risk when exposed to sustained ambient noise levels higher than 60 dBA. These same studies have also linked ambient indoor noise levels from outdoor road noise to increases in hypertension. These types of studies frequently rely on self-reporting of noise levels and symptoms, so the inclusion of a microphone may allow for the objective assessment of noise levels. Finally, the microphones may be used for communication with the clinical team. When an audio or video call is initiated between the patient and clinical team, the patient can conduct the call directly from the hub, again removing any dependence on the patient's own phone or technology.

Figure 8:
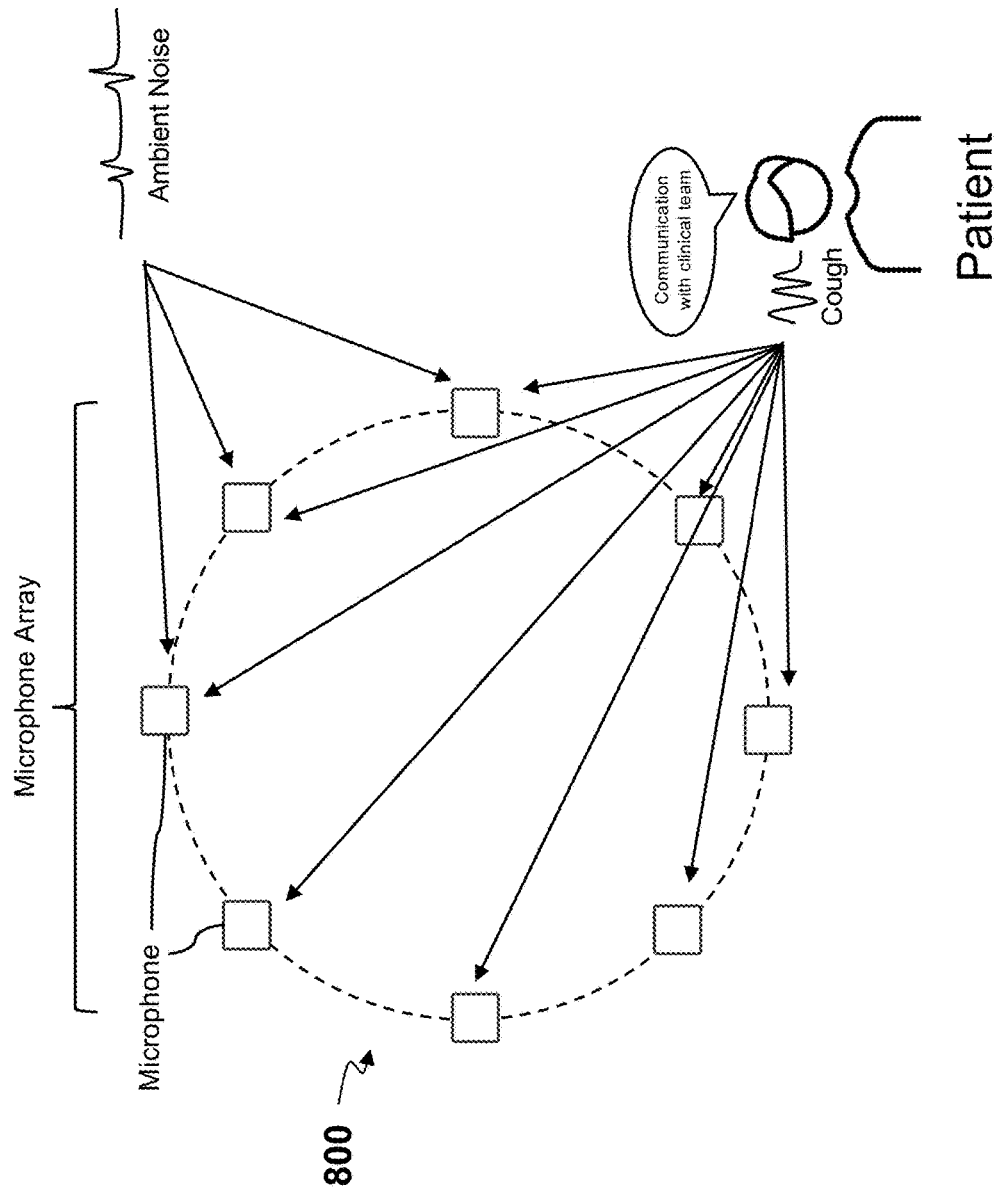
FIG. 8 depicts a microphone array included in a medical hub, according to one embodiment.

FIG. 8 depicts a microphone array 800 included in a medical hub, according to one embodiment. As depicted, the microphone array 800 may comprise a plurality of matched microphones arranged in a circular array. The array of plurality microphones may be necessary for beamforming to understand the direction of arrival, distance, and ambient noise estimation, as all have been shown to impact the accuracy of these types of algorithms. Processing of the acoustic signals may be done in real-time and onboard the hub, as previously discussed, to ensure the privacy of recordings. Both array beamforming and local processing of acoustic signals may be implemented by the disclosed system embodiments.

The disclosed system is configured to provide Cybersecurity & Privacy data protection and secure data from unauthorized use or access. It is estimated that approximately half of IoT medical devices may be at risk of being exposed to data theft or other cybersecurity risks. Similarly, IoT devices have been at the center of several large cyber-attacks, which may include a system that employs thousands of unsecured IoT gateways and devices to conduct distributed denial of service (DDOS) attacks. The hub may include several cybersecurity technologies in order to secure the highly sensitive data that is being collected and transmitted to and from the patient.

The Application Processor, the processor running on the hub's hardware, may be configured to implement trusted execution, root-of-trust, and secure key storage security features. The system may also implement hardware-accelerated cryptography and a key management unit (KMU). The system may implement several techniques to monitor data activity and packets, including a traffic analyzer that may filter or block unusual behavior and traffic from untrusted sources, latency examination, packet inspection, and traffic categorization. All data may be encrypted and sent over a secure connection, and no identifiable patient information is stored on the hub; all data may be tagged using randomly generated, unique patient IDs.

The Bluetooth Network Processor may also be heavily restricted to reduce the risk of possible attacks including, for example, Bluesnarfing, Bluejacking, and Blue bugging. By connecting to medical devices via a secured gateway rather than allowing medical devices to connect directly to the outside world like in some existing systems, the disclosed system may reduce vector of attack for these Bluetooth devices.

The system may be configured to be updated as new features, bug fixes, or security patches need to be implemented. System firmware may be updated using a secure process, including source verification and code signing.

These updates may allow for updating security features, privacy features, and updating functionality. For example, as new algorithms are developed that run locally on the hub rather than in the cloud system, they may be installed on the hub via over-the-air (OTA) software updates.

Embodiments of the disclosed system may include edge computing, local data storage and processing, and threshold analysis and notification components. An optional dedicated neural network accelerator chip for onboard analysis is also disclosed. Additionally, the system may include data processing on a processor, where the processor may include dedicated machine learning hardware, which may be included with a purpose-built neural network accelerator.

Other features and embodiments may include:
Solutions that leverage phones, tablets, or computers as gateways rather than standalone systems.
An integrated display, camera, and microphone array that is used for voice and video calls with clinical teams.
The use of a microphone array for abnormality detection, used for beamforming and noise removal.
The ability to maintain multiple simultaneous connections to medical devices and automatic connections to medical devices when in use.
Automated device setup and configuration.
Specific cybersecurity and privacy measures that are included in the system.

The disclosed embodiments implement a set of functionalities when dealing with low-bandwidth situations. Specifically, the use of network selection logic to select the optimal connection and technology from multiple carriers is disclosed, where the architecture for cellular connectivity does not require dedicated hardware for each cellular provider, which is not easily interchangeable.

In some embodiments, the system may include edge computing by dedicated processors, local database management, and local threshold analysis and notification modules, thereby providing a system that is configured to correlate between environmental factors and symptoms in patients and show environmental data points via objective environmental data that can clearly correlate with real-time symptoms. That is, environmental data may be collected and used to contextualize abnormal biological data, such as heart rate or respiratory rate, to improve patient care.

Figure 9:
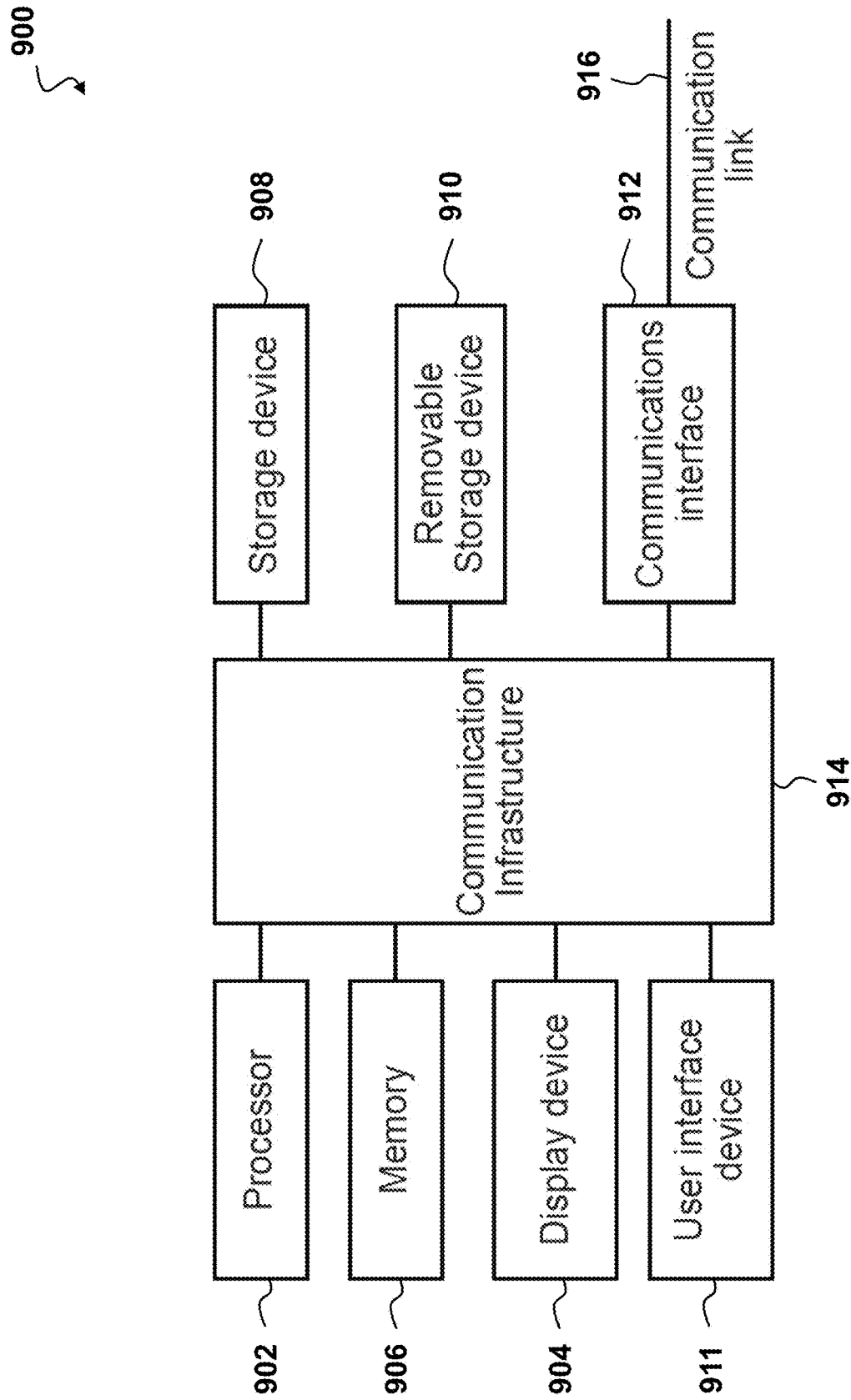
FIG. 9 shows a high-level block diagram and process of a computing system for implementing an embodiment of the system and process.

FIG. 9 is a high-level block diagram 900 showing a computing system comprising a computer system useful for implementing an embodiment of the system and process, disclosed herein. Embodiments of the system may be implemented in different computing environments. The computer system includes one or more processors 902, and can further include an electronic display device 904 (e.g., for displaying graphics, text, and other data), a main memory 906 (e.g., random access memory (RAM)), storage device 908, a removable storage device 910 (e.g., removable storage drive, a removable memory module, a magnetic tape drive, an optical disk drive, a computer-readable medium having stored therein computer software and/or data), a user interface device 911 (e.g., keyboard, touch screen, keypad, pointing device), and a communication interface 912 (e.g., modem, a network interface (such as an Ethernet card), a communications port, or a PCMCIA slot and card). The communication interface 912 allows software and data to be transferred between the computer system and external devices. The system further includes a communication infrastructure 914 (e.g., a communications bus, cross-over bar, or network) to which the aforementioned devices/modules are connected, as shown.

Information transferred via communications interface 912 may be in the form of signals such as electronic, electromagnetic, optical, or other signals capable of being received by communications interface 912, via a communication link 916 that carries signals and may be implemented using wire or cable, fiber optics, a phone line, a cellular/mobile phone link, a radio frequency (RF) link, and/or other communication channels. Computer program instructions representing the block diagram and/or flowcharts herein may be loaded onto a computer, programmable data processing apparatus, or processing devices to cause a series of operations performed thereon to produce a computer-implemented process.

Embodiments have been described with reference to flowchart illustrations and/or block diagrams of methods, apparatus (systems) and computer program products according to embodiments. Each block of such illustrations/diagrams, or combinations thereof, can be implemented by computer program instructions. The computer program instructions when provided to a processor produce a machine, such that the instructions, which execute via the processor, create means for implementing the functions/operations specified in the flowchart and/or block diagram. Each block in the flowchart/block diagrams may represent a hardware and/or software module or logic, implementing embodiments. In alternative implementations, the functions noted in the blocks may occur out of the order noted in the figures, concurrently, etc.

Computer programs (i.e., computer control logic) are stored in main memory and/or secondary memory. Computer programs may also be received via a communications interface 912. Such computer programs, when executed, enable the computer system to perform the features of the embodiments as discussed herein. In particular, the computer programs, when executed, enable the processor and/or multi-core processor to perform the features of the computer system. Such computer programs represent controllers of the computer system.

Figure 10:
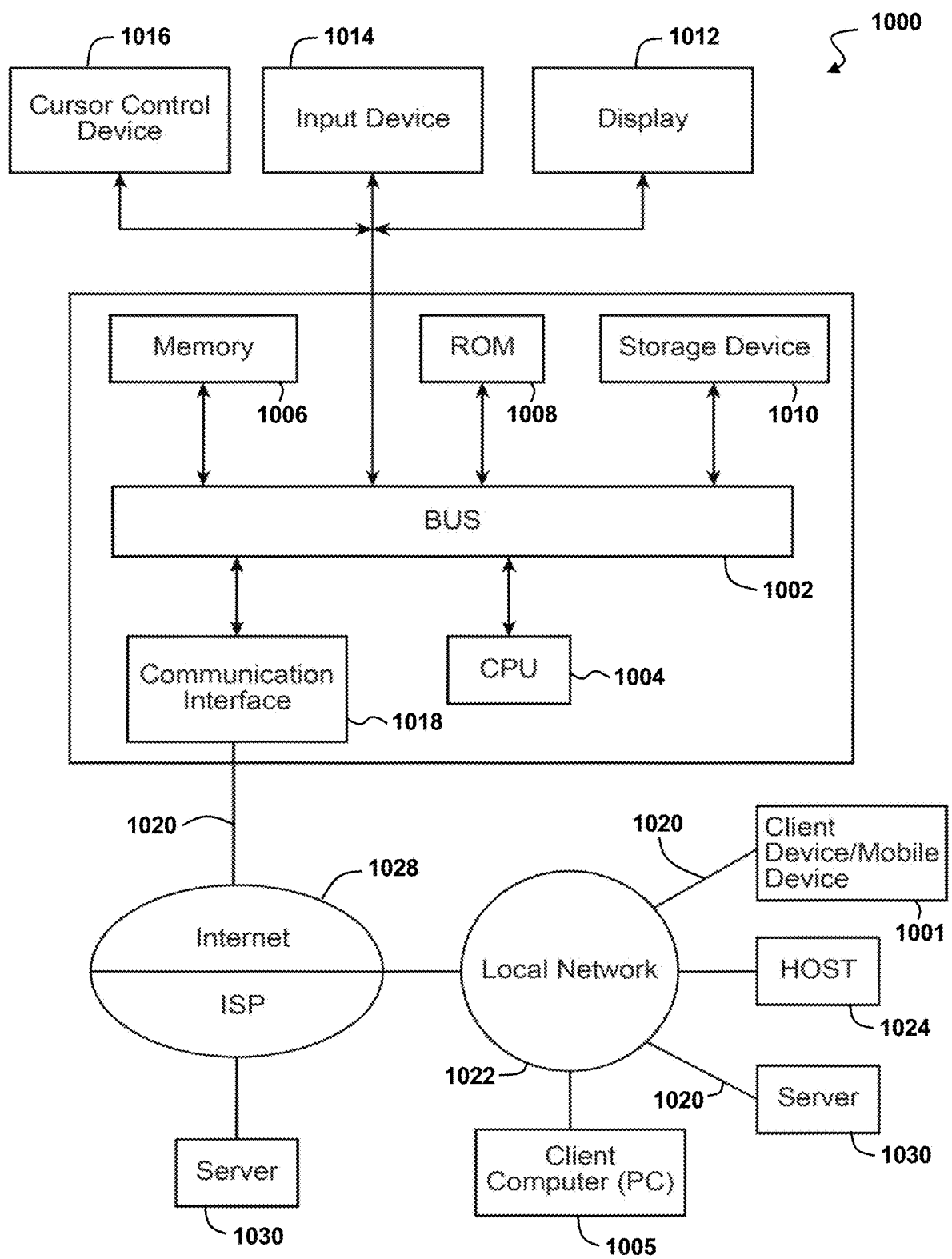
FIG. 10 shows a block diagram and process of an exemplary system in which an embodiment may be implemented.

FIG. 10 shows a block diagram of an example system 1000 in which an embodiment may be implemented. The system 1000 includes one or more client devices 1001 such as consumer electronics devices, connected to one or more server computing systems 1030. A server 1030 includes a bus 1002 or other communication mechanism for communicating information, and a processor (CPU) 1004 coupled with the bus 1002 for processing information. The server 1030 also includes a main memory 1006, such as a random access memory (RAM) or other dynamic storage device, coupled to the bus 1002 for storing information and instructions to be executed by the processor 1004. The main memory 1006 also may be used for storing temporary variables or other intermediate information during execution or instructions to be executed by the processor 1004. The server computer system 1030 further includes a read-only memory (ROM) 1008 or other static storage device coupled to the bus 1002 for storing static information and instructions for the processor 1004. A storage device 1010, such as a magnetic disk or optical disk, is provided and coupled to the bus 1002 for storing information and instructions. The bus 1002 may contain, for example, thirty-two address lines for addressing video memory or main memory 1006. The bus 1002 can also include, for example, a 32-bit data bus for transferring data between and among the components, such as the CPU 1004, the main memory 1006, video memory and the storage 1010. Alternatively, multiplex data/address lines may be used instead of separate data and address lines.

The server 1030 may be coupled via the bus 1002 to a display 1012 for displaying information to a computer user. An input device 1014, including alphanumeric and other keys, is coupled to the bus 1002 for communicating information and command selections to the processor 1004. Another type of user input device comprises cursor control 1016, such as a mouse, a trackball, or cursor direction keys for communicating direction information and command selections to the processor 1004 and for controlling cursor movement on the display 1012.

According to one embodiment, the functions are performed by the processor 1004 executing one or more sequences of one or more instructions contained in the main memory 1006. Such instructions may be read into the main memory 1006 from another computer-readable medium, such as the storage device 1010. Execution of the sequences of instructions contained in the main memory 1006 causes the processor 1004 to perform the process steps described herein. One or more processors in a multi-processing arrangement may also be employed to execute the sequences of instructions contained in the main memory 1006. In alternative embodiments, hard-wired circuitry may be used in place of or in combination with software instructions to implement the embodiments. Thus, embodiments are not limited to any specific combination of hardware circuitry and software.

The terms "computer program medium," "computer usable medium," "computer-readable medium", and "computer program product" are used to generally refer to media such as main memory, secondary memory, removable storage drive, a hard disk installed in hard disk drive, and signals. These computer program products are means for providing software to the computer system. The computer-readable medium allows the computer system to read data, instructions, messages or message packets, and other computer-readable information from the computer-readable medium. The computer-readable medium, for example, may include non-volatile memory, such as a floppy disk, ROM, flash memory, disk drive memory, a CD-ROM, and other permanent storage. It is useful, for example, for transporting information, such as data and computer instructions, between computer systems. Furthermore, the computer-readable medium may comprise computer-readable information in a transitory state medium such as a network link and/or a network interface, including a wired network or a wireless network that allows a computer to read such computer-readable information. Computer programs (also called computer control logic) are stored in main memory and/or secondary memory. Computer programs may also be received via a communications interface. Such computer programs, when executed, enable the computer system to perform the features of the embodiments as discussed herein. In particular, the computer programs, when executed, enable the processor multi-core processor to perform the features of the computer system. Accordingly, such computer programs represent controllers of the computer system.

Generally, the term "computer-readable medium," as used herein, refers to any medium that participated in providing instructions to the processor 1004 for execution. Such a medium may take many forms, including, but not limited to, non-volatile media, volatile media, and transmission media. Non-volatile media includes, for example, optical or magnetic disks, such as the storage device 1010. Volatile media includes dynamic memory, such as the main memory 1006. Transmission media includes coaxial cables, copper wire, and fiber optics, including the wires that comprise the bus 1002. Transmission media can also take the form of acoustic or light waves, such as those generated during radio waves and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, an EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1004 for execution. For example, the instructions may initially be carried on a magnetic disk of a remote computer. The remote computer can load the instructions into its dynamic memory and send the instructions over a telephone line using a modem. A modem local to the server 1030 can receive the data on the telephone line and use an infrared transmitter to convert the data to an infrared signal. An infrared detector coupled to the bus 1002 can receive the data carried in the infrared signal and place the data on the bus 1002. The bus 1002 carries the data to the main memory 1006, from which the processor 1004 retrieves and executes the instructions. The instructions received from the main memory 1006 may optionally be stored on the storage device 1010 either before or after execution by the processor 1004.

The server 1030 also includes a communication interface 1018 coupled to the bus 1002. The communication interface 1018 provides a two-way data communication coupling to a network link 1020 that is connected to the worldwide packet data communication network now commonly referred to as the Internet 1028. The Internet 1028 uses electrical, electromagnetic, or optical signals that carry digital data streams. The signals through the various networks and the signals on the network link 1020 and through the communication interface 1018, which carry the digital data to and from the server 1030, are exemplary forms of carrier waves transporting the information.

In another embodiment of the server 1030, interface 1018 is connected to a network 1022 via a communication link 1020. For example, the communication interface 1018 may be an integrated services digital network (ISDN) card or a modem to provide a data communication connection to a corresponding type of telephone line, which can comprise part of the network link 1020. As another example, the communication interface 1018 may be a local area network (LAN) card to provide a data communication connection to a compatible LAN. Wireless links may also be implemented. In any such implementation, the communication interface 1018 sends and receives electrical electromagnetic or optical signals that carry digital data streams representing various types of information.

The network link 1020 typically provides data communication through one or more networks to other data devices. For example, the network link 1020 may provide a connection through the local network 1022 to a host computer 1024 or to data equipment operated by an Internet Service Provider (ISP). The ISP, in turn, provides data communication services through the Internet 1028. The local network 1022 and the Internet 1028 both use electrical, electromagnetic, or optical signals that carry digital data streams. The signals through the various networks and the signals on the network link 1020 and through the communication interface 1018, which carry the digital data to and from the server 1030, are exemplary forms of carrier waves transporting the information.

The server 1030 can send/receive messages and data, including e-mail and program code, through the network, the network link 1020, and the communication interface 1018. Further, the communication interface 1018 can comprise a USB/Tuner, and the network link 1020 may be an antenna or cable for connecting the server 1030 to a cable provider, satellite provider, or other terrestrial transmission system for receiving messages, data, and program code from another source.

The example versions of the embodiments described herein may be implemented as logical operations in a distributed processing system such as the system 1000 including the servers 1030. The logical operations of the embodiments may be implemented as a sequence of steps executing in the server 1030, and as interconnected machine modules within the system 1000. The implementation is a matter of choice and can depend on the performance of the system 1000 implementing the embodiments. As such, the logical operations constituting said example versions of the embodiments are referred to, for e.g., as operations, steps, or modules.

Similar to a server 1030 described above, a client device 1001 can include a processor, memory, storage device, display, input device, and communication interface (e.g., e-mail interface) for connecting the client device to the Internet 1028, the ISP, or LAN 1022, for communication with the servers 1030.

The system 1000 can further include computers (e.g., personal computers, computing nodes) 1005 operating in the same manner as client devices 1001, where a user can utilize one or more computers 1005 to manage data in the server 1030.

Figure 11:
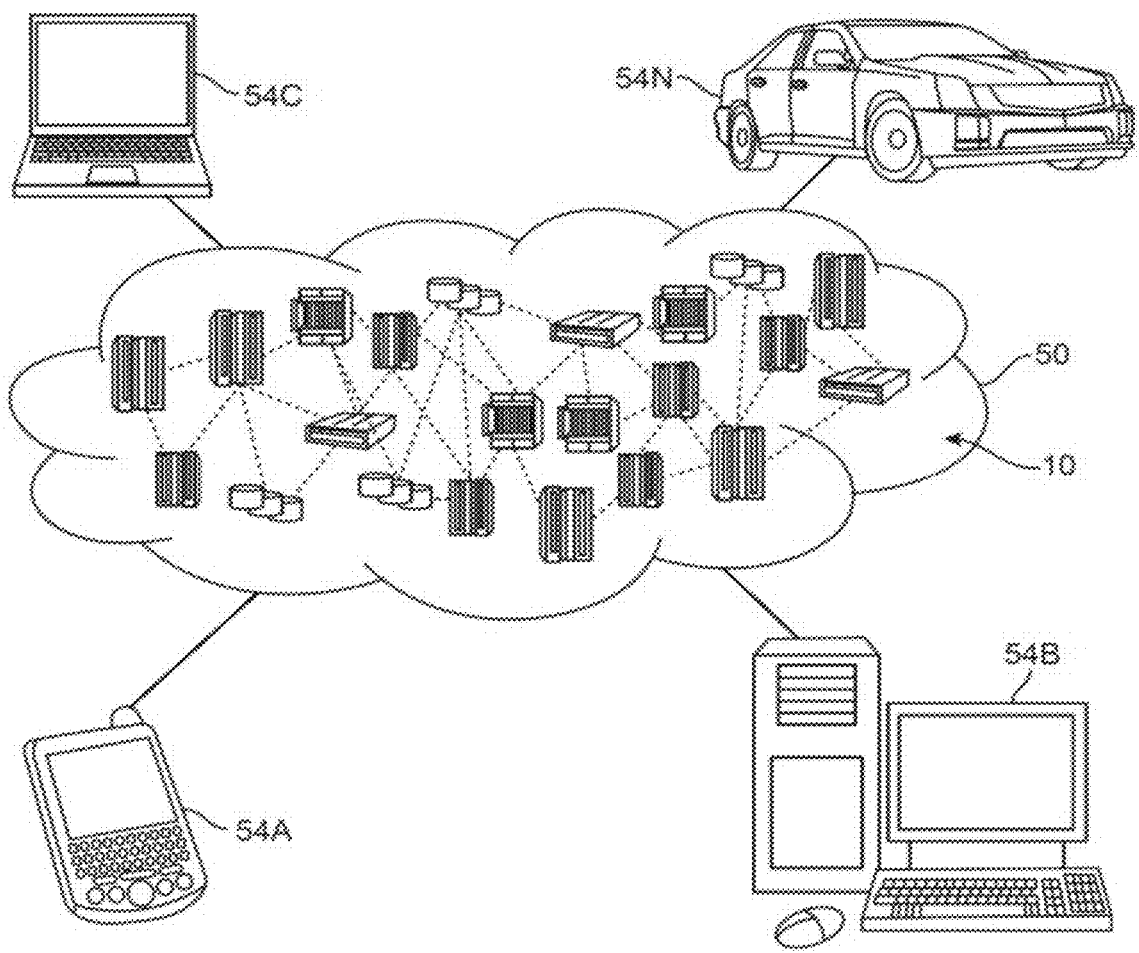
FIG. 11 depicts a cloud computing environment for implementing an embodiment of the system and process disclosed herein.

Referring now to FIG. 11, illustrative computing environment 1100 is depicted. As shown, cloud computing environment 50 comprises one or more cloud computing nodes 10 with which local computing devices used by cloud consumers, such as, for example, personal digital assistant (PDA), smartphone, smartwatch, set-top box, video game system, tablet, mobile computing device, or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 11 are intended to be illustrative only and that computing nodes 10 and cloud computing environment 50 can communicate with any type of computerized device over any type of network and/or network addressable connection (e.g., using a web browser).

Figure 12:
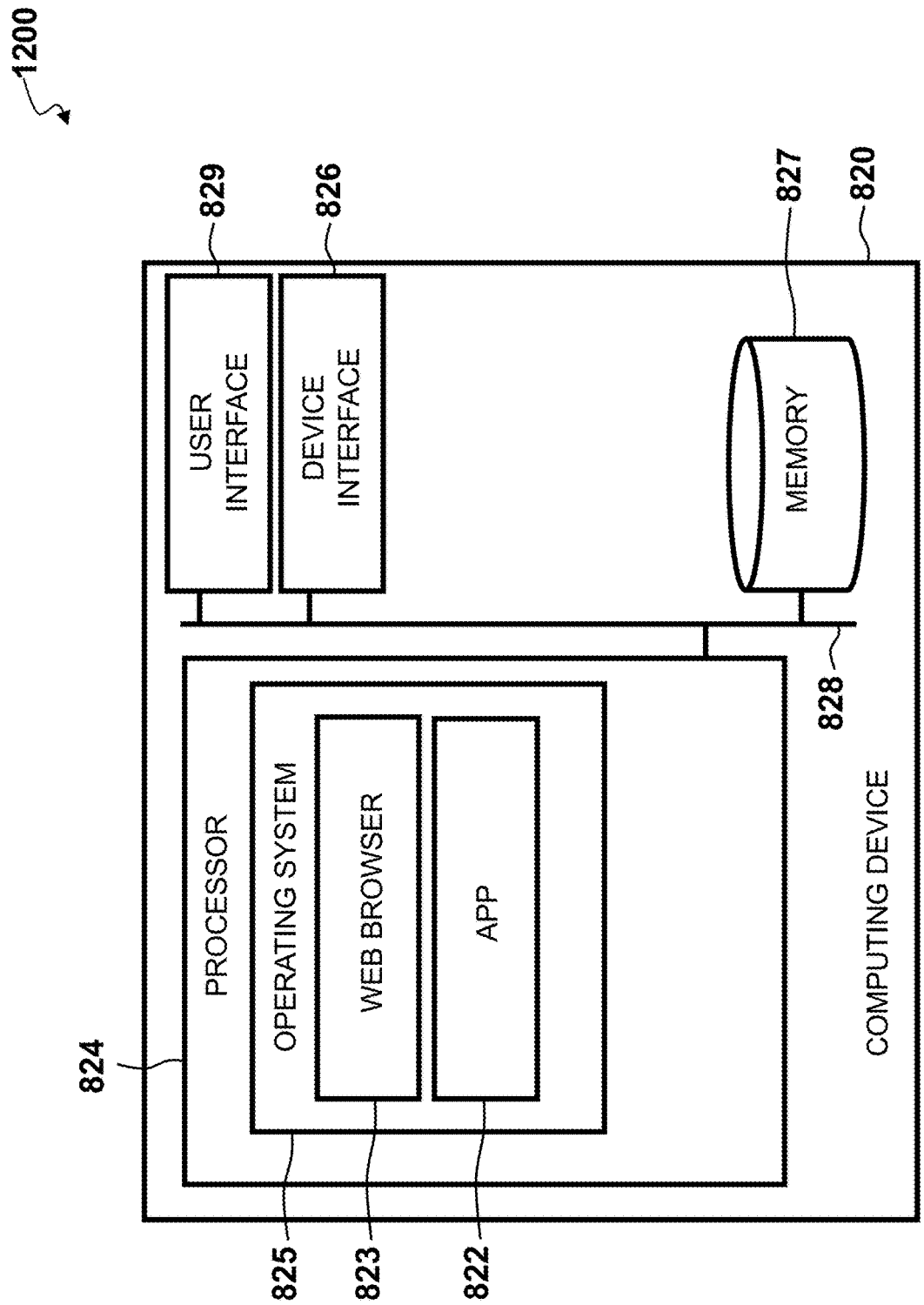
FIG. 12 illustrates an example top-level functional block diagram of a computing device embodiment.

FIG. 12 illustrates an example of a top-level functional block diagram of a computing device embodiment 1200. The example operating environment is shown as a computing device 820 comprising a processor 824, such as a central processing unit (CPU), addressable memory 827, an external device interface 826, e.g., an optional universal serial bus port and related processing, and/or an Ethernet port and related processing, and an optional user interface 829, e.g., an array of status lights and one or more toggle switches, and/or a display, and/or a keyboard and/or a pointer-mouse system and/or a touch screen. Optionally, the addressable memory may include any type of computer-readable media that can store data accessible by the computing device 820, such as magnetic hard and floppy disk drives, optical disk drives, magnetic cassettes, tape drives, flash memory cards, digital video disks (DVDs), Bernoulli cartridges, RAMs, ROMs, smart cards, etc. Indeed, any medium for storing or transmitting computer-readable instructions and data may be employed, including a connection port to or node on a network, such as a LAN, WAN, or the Internet. These elements may be in communication with one another via a data bus 828. In some embodiments, via an operating system 825, such as one supporting a web browser 823 and applications 822, the processor 824 may be configured to execute steps of a process establishing a communication channel and processing according to the embodiments described above.

It is contemplated that various combinations and/or subcombinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further, it is intended that the scope of the present invention is herein disclosed by way of examples and should not be limited by the particular disclosed embodiments described above.

What is claimed is:

1. A system comprising:
   an Internet of Things (IoT) secured gateway;
   a user interface comprising an interactivity tool;
   an environmental monitoring device configured to collect environmental data;
   a set of sensors configured to collect biological signals;
   a secure encrypted local database; and
   a medical hub device comprising a processor and addressable memory;
   wherein the system is configured to:
   collect, via the set of sensors, biological signals related to patient status, wherein the biological signals are collected on a continual basis;
   collect, via the environmental monitoring device, environmental data associated with patient environment and used for monitoring patient status, wherein the environmental data are collected on a continual basis;
   store, locally via the secure encrypted local database, the collected biological signals and the collected environmental data spanning over a period of time;
   detect, by the processor, an abnormality in the collected biological signals based on comparing the collected biological signals of a current reading versus the locally stored biological signals representing a prior reading, wherein the abnormality detection is executed for biological signals collected by all the sensors in the set of sensors;
   increase, by the processor, measurement frequency of the biological signals by the set of sensors based on the detected abnormality to determine whether the detected abnormality of the collected biological signal sensor reading with the increased frequency measurements is consistent across sequentially collected biological signals;
   detect, by the processor, an error in the collected biological signals of the current reading with the increased frequency measurements based on comparing collected biological signals of an alternate sensor of the set of sensors versus locally stored biological signals representing a prior reading by the alternate sensor of the set of sensors, thereby detection of an abnormality by the alternate sensor indicates that the detected abnormality is due to a sensor error;
   determine, by the processor, whether the detected error in the collected biological signals of the current reading is due to environmental factors based on correlating the collected environmental data with the collected biological signal;
   correct, by the processor, the determined error in the collected biological signals by prioritizing the detected abnormality based on the correlated collected biological signals and the collected environmental data; and
   transmit, via the IoT secured gateway, the error corrected collected biological signals as encrypted data over a secure connection to a cloud system.

2. The system of claim 1, further comprising a dedicated neural network accelerator chip for on-board analysis, wherein data points from the collected data including at least one of the biological signals and the environmental data are extracted and only such data points are stored wherein other identifiable patient information is discarded.

3. The system of claim 2, wherein values of the extracted data point are non-linear transformations of the collected data, and therefore an original recording of the collected biological signals cannot be reconstructed from these values.

4. The system of claim 3, wherein the dedicated neural network accelerator hardware allows the collecting and monitoring to be always on without impacting privacy.

5. The system of claim 1, wherein the environmental monitoring device comprises at least one of: a particulate matter sensor, an environmental sensor, an air quality sensor, and an ambient light sensor.

6. The system of claim 5, wherein the particulate matter sensor is configured to use optical technology to detect particulate matter.

7. The system of claim 5, wherein the environmental sensor is configured to measure at least one of temperature, humidity, and pressure.

8. The system of claim 5, wherein the air quality sensor is configured to measure at least one of volatile organic compounds (VOCs), volatile sulfur compounds (VSCs), carbon monoxide (ACO), and hydrogen.

9. The system of claim 5, wherein the ambient light sensor includes a set of photodiodes in a single package configured to measure ambient light levels.

10. The system of claim 1, further comprising a microphone array, wherein the microphone array is configured to monitor coughing frequency and cough characteristics.

11. The system of claim 10, wherein in order to remove privacy risks, data points including at least one of cough counts, cough features, and noise levels are extracted on the medical hub device, and only those extracted data points are stored and telemetered while the full audio recordings from the microphone array are discarded.

12. The system of claim 1, wherein the system is further configured to:
   transmit, via the user interface, a message to indicate that a sensor error has been detected based on a determination that the detected abnormality is caused by a sensor error.

13. The system of claim 12, wherein the system is further configured to:
   notify, via the user interface, a patient in real-time without waiting for roundtrip transmission time for communication to be transmitted to a clinical team, thereby avoid unnecessary bidirectional communication between the medical hub device and the cloud system.

14. The system of claim 1, wherein an error is detected if measurement data of the collected biological signals are outside of bounds set by a clinical team.

15. The system of claim 1, wherein if the system is not able to perform error correction, then the system is configured to: transmit a notification to a patient to be notified in real-time from the medical hub device rather than waiting for round trip transit time for the medical hub device to communicate the measurement data to the clinical team via the cloud system.

16. The system of claim 1, wherein no identifiable patient information is stored locally in the secure encrypted local database and all data is tagged using randomly generated unique patient IDs for remote patient monitoring thereby avoiding unnecessary bidirectional communication between the system and the cloud system.

17. A device comprising:
a processor and addressable memory, the device configured to:
receive, from a set of sensors, collected biological signals related to patient status, wherein the biological signals are collected on a continual basis;
receive, from an environmental monitoring device, collected environmental data associated with patient environment and used for monitoring patient status, wherein the environmental data are collected on a continual basis;
store, locally via a secure encrypted local database, the collected biological signals and the collected environmental data spanning over a period of time;
detect, by the processor, an abnormality in the collected biological signals based on comparing the collected biological signals of a current reading versus the locally stored biological signals representing a prior reading, wherein the abnormality detection is executed for biological signals collected by all the sensors in the set of sensors;
increase, by the processor, measurement frequency of the biological signals by the set of sensors based on the detected abnormality to determine whether the detected abnormality of the collected biological signal sensor reading with the increased frequency measurements is consistent across sequentially collected biological signals;
detect, by the processor, an error in the collected biological signals of the current reading with the increased frequency measurements based on comparing collected biological signals of an alternate sensor of the set of sensors versus locally stored biological signals representing a prior reading by the alternate sensor of the set of sensors, thereby detection of an abnormality by the alternate sensor indicates that the detected abnormality is due to a sensor error;
determine, by the processor, whether the detected error in the collected biological signals of the current reading is due to environmental factors based on correlating the collected environmental data with the collected biological signal;
correct, by the processor, the determined error in the collected biological signals by prioritizing the detected abnormality based on the correlated collected biological signals and the collected environmental data; and
transmit, via an Internet of Things (IoT) secured gateway, the error corrected collected biological signals as encrypted data over a secure connection to a cloud system.

18. A method comprising:
collecting, via a set of sensors, biological signals related to patient status, wherein the biological signals are collected on a continual basis;
collecting, via an environmental monitoring device, environmental data associated with patient environment and used for monitoring patient status, wherein the environmental data are collected on a continual basis;
storing, locally via a secure encrypted local database, the collected biological signals and the collected environmental data spanning over a period of time;
detecting, by a medical hub device, an abnormality in the collected biological signals based on comparing the collected biological signals of a current reading versus the locally stored biological signals representing a prior reading, wherein the abnormality detection is executed for biological signals collected by all the sensors in the set of sensors;
increasing, by the device, measurement frequency of the biological signals by the set of sensors based on the detected abnormality to determine whether the detected abnormality of the collected biological signal sensor reading with the increased frequency measurements is consistent across sequentially collected biological signals;
detecting, by the device, an error in the collected biological signals of the current reading with the increased frequency measurements based on comparing collected biological signals of an alternate sensor of the set of sensors versus locally stored biological signals representing a prior reading by the alternate sensor of the set of sensors, thereby detection of an abnormality by the alternate sensor indicates that the detected abnormality is due to a sensor error;
determining, by the device, whether the detected error in the collected biological signals of the current reading is due to environmental factors based on correlating the collected environmental data with the collected biological signal;
correcting, by the device, the determined error in the collected biological signals by prioritizing the detected abnormality based on the correlated collected biological signals and the collected environmental data; and
transmitting, by the device, the error corrected collected biological signals as encrypted data over a secure connection to a cloud system.

\* \* \* \* \*